US008504140B2

(12) United States Patent
Feke et al.

(10) Patent No.: US 8,504,140 B2
(45) Date of Patent: *Aug. 6, 2013

(54) APPARATUS AND METHOD FOR FLUORESCENCE IMAGING AND TOMOGRAPHY USING SPATIALLY STRUCTURED ILLUMINATION

(75) Inventors: Gilbert Feke, Durham, CT (US); Laurie L. Voci, Victor, NY (US)

(73) Assignee: Bruker BioSpin Corporation, Billerica, MA (US)

( * ) Notice: Subject to any disclaimer, the term of this patent is extended or adjusted under 35 U.S.C. 154(b) by 857 days.

This patent is subject to a terminal disclaimer.

(21) Appl. No.: 12/411,432

(22) Filed: Mar. 26, 2009

(65) Prior Publication Data

US 2009/0250631 A1 Oct. 8, 2009

Related U.S. Application Data

(60) Provisional application No. 61/043,188, filed on Apr. 8, 2008.

(51) Int. Cl.
*A61B 6/02* (2006.01)
(52) U.S. Cl.
USPC .................................. 600/476; 250/458.1

(58) Field of Classification Search
USPC .................................. 600/476; 250/458.1
See application file for complete search history.

(56) References Cited

U.S. PATENT DOCUMENTS

| 7,612,805 B2 * | 11/2009 | Solomon ..................... 348/222.1 |
| 7,994,485 B2 * | 8/2011 | Feke et al. ................... 250/458.1 |
| 2003/0010930 A1 | 1/2003 | Thorwirth | |
| 2006/0184043 A1 | 8/2006 | Tromberg et al. | |

* cited by examiner

*Primary Examiner* — Tse Chen
*Assistant Examiner* — Vani Gupta
(74) *Attorney, Agent, or Firm* — O'Shea Getz P.C.

(57) ABSTRACT

An imaging system for imaging an object. More specifically, an imaging system enabling depth sectioned fluorescence imaging in a turbid medium, such as human or animal tissue, to substantially minimize the excitation radiation from reaching the detection beam path. The imaging system includes an arrangement of the excitation radiation source wherein the optical axis of the source is inclined relative to the optical axis of the camera, the optical plane of the source and the optical plane of the object are subject to a Scheimpflug condition, and the angle of inclination of the source is selected such that the excitation radiation incident upon the object is reflected to minimize excitation radiation from reaching the detection beam path.

22 Claims, 35 Drawing Sheets

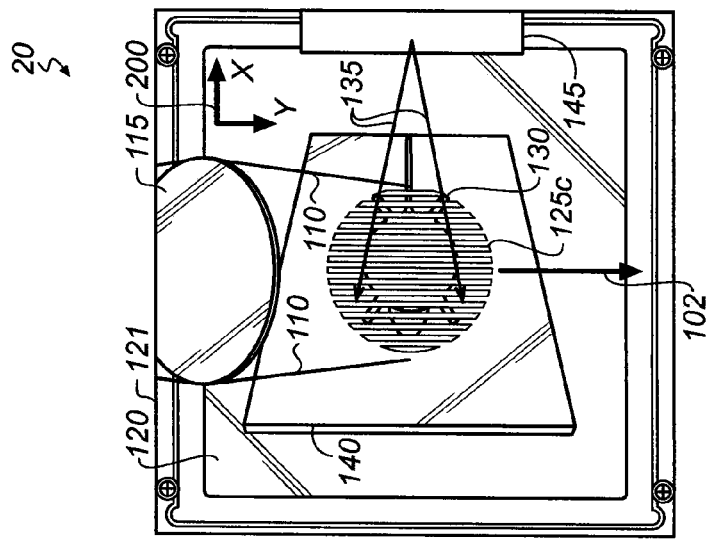
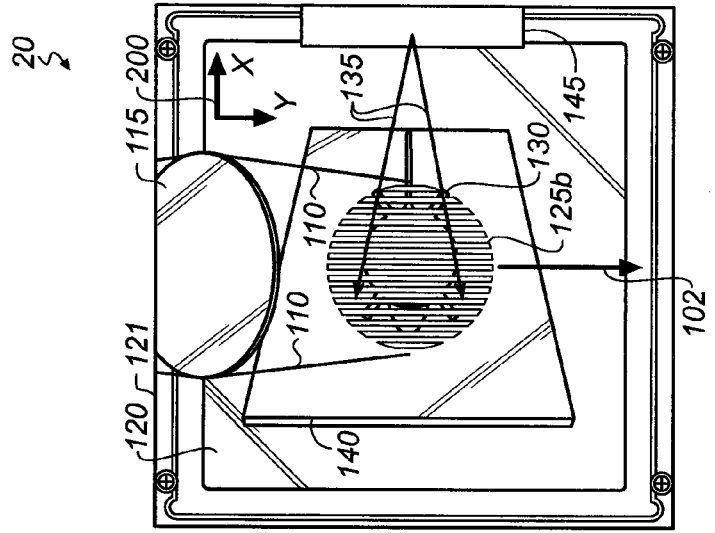
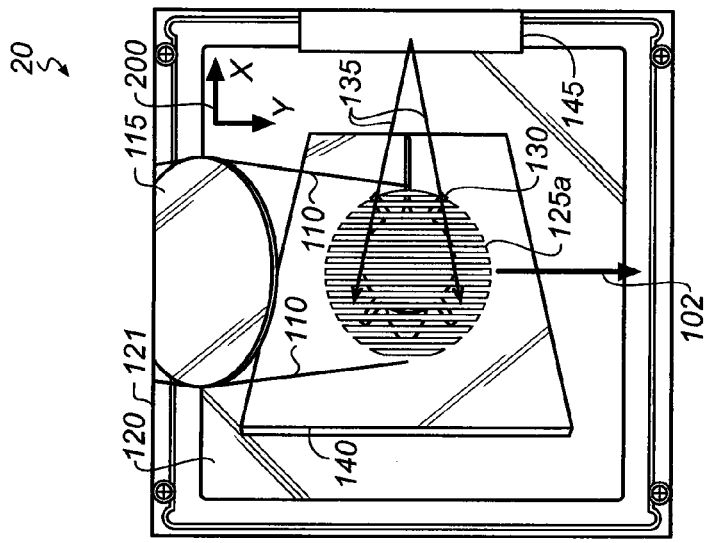

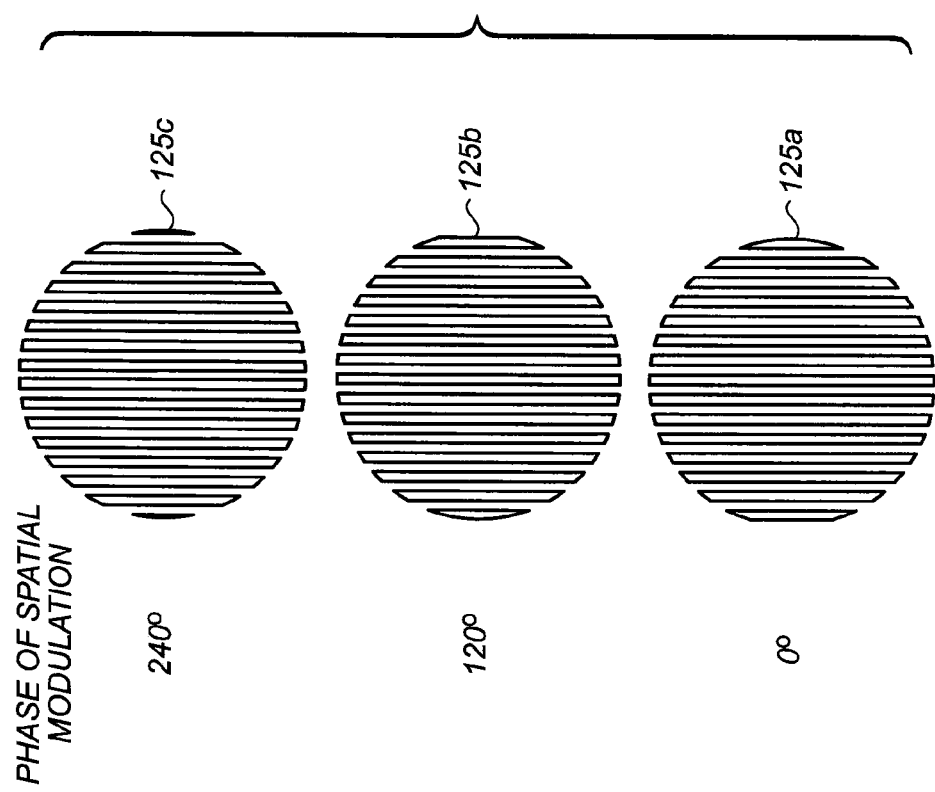

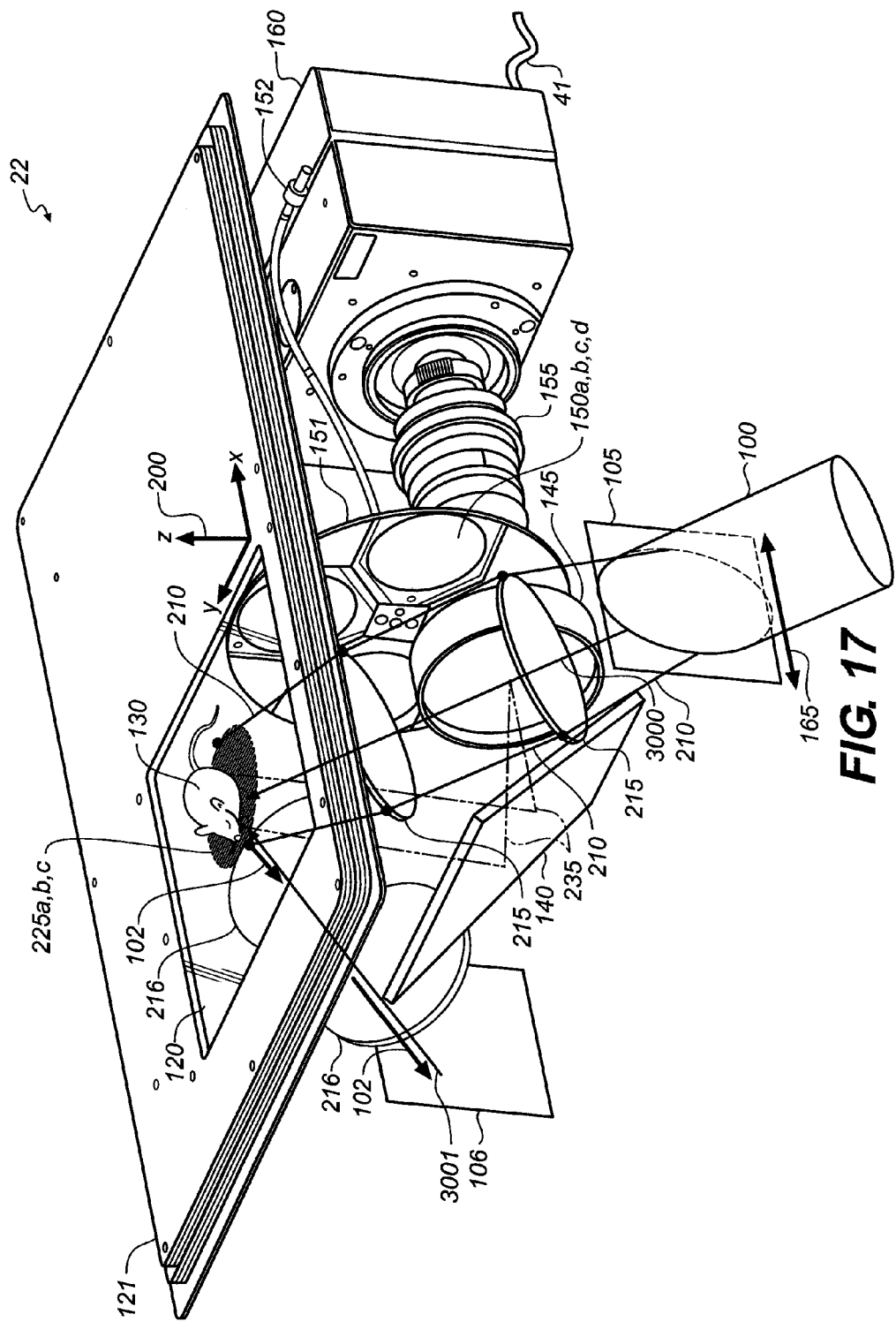

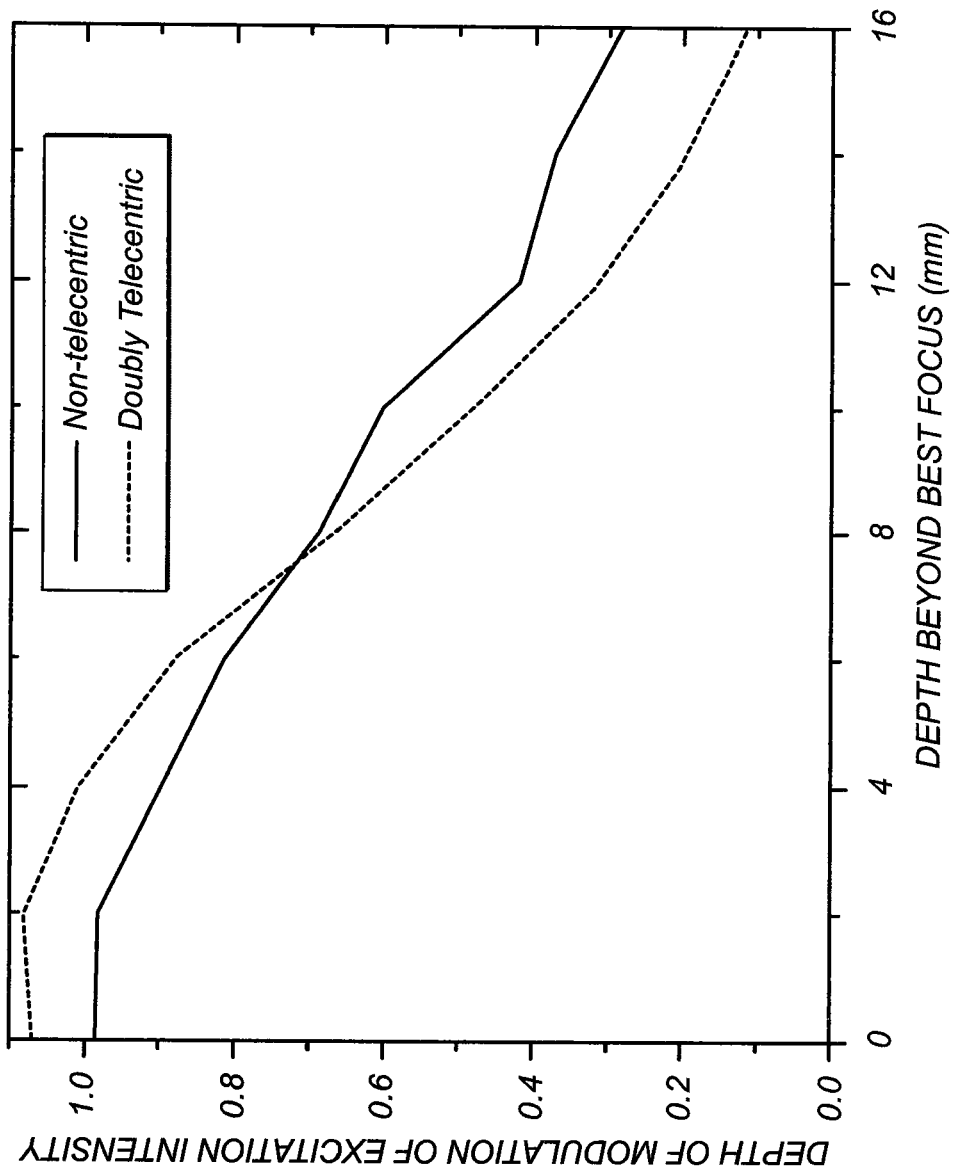

APPARATUS AND METHOD FOR FLUORESCENCE IMAGING AND TOMOGRAPHY USING SPATIALLY STRUCTURED ILLUMINATION

CROSS REFERENCE TO RELATED APPLICATIONS

Reference is made to, and priority is claimed from, commonly assigned, provisional U.S. patent application Ser. No. 61/043,188, filed Apr. 8, 2008 by Gilbert Feke, entitled APPARATUS AND METHOD FOR FLUORESCENCE IMAGING AND TOMOGRAPHY USING SPATIALLY STRUCTURED ILLUMINATION, which is incorporated by reference.

FIELD OF THE INVENTION

The invention relates generally to the field of imaging systems, and more particularly to the imaging of objects. More specifically, the invention relates to an improvement in an apparatus and method enabling depth sectioned fluorescence imaging in a turbid medium, such as human or animal tissue, in such a manner as to substantially minimize the excitation radiation from reaching the detection beam path.

BACKGROUND OF THE INVENTION

It is well known in the art to use structured illumination to carry out fluorescence-based molecular imaging in turbid media. U.S. Publication 2006/0184043 by Tromberg et al. (Tromberg) discloses a method for quantitative modulated imaging to perform depth sectioned reflectance or transmission imaging in a turbid medium, such as human or animal tissue. The method is directed to steps of encoding periodic pattern of illumination preferably with a fluorescent excitation wavelength when exposing a turbid medium to the periodic pattern to provide depth-resolved discrimination of structures within the turbid medium; and reconstructing a non-contact three dimensional image of the structure within a turbid medium. As a result, Tromberg states that wide field imaging, separation of the average background optical properties from the heterogeneity components from a single image, separation of superficial features from deep features based on selection of spatial frequency of illumination, or qualitative and quantitative structure, function and composition information may be extracted from spatially encoded data. However, Tromberg does not teach how to minimize the excitation radiation from reaching the detection beam path.

U.S. Publication 2003/0010930 by Thorwirth discloses an arrangement for reading out the fluorescent radiation of specimen carriers with a plurality of individual specimens which for purposes of exciting fluorescent radiation in selected individual specimens comprises a switchable electro-optical matrix for generating illumination which is limited in a spatially defined manner. An arrangement is disclosed for reading out the fluorescent radiation of selected individual specimens of multispecimen carriers having a switchable electro-optical matrix for generating illumination which is limited in a spatially defined manner, an optical system for imaging the electro-optical matrix on the specimen carrier, and a high-sensitivity photoreceiver for integral measurement of the fluorescent radiation of the excited individual specimens of the specimen carrier. Thorwirth discloses a spatially differentiated illumination of a specimen carrier with a plurality of specimens using an electro-optical matrix which minimizes the proportion of excitation radiation contributing to the fluorescence signal in high-resolution imaging. The electro-optical matrix and the specimen carrier are inclined relative to the optical axis of the optical system and are subject to a Scheimpflug condition. The angles of inclination of the electro-optical matrix and of the specimen carrier are selected such that the excitation radiation imaged by the light source unit on the specimen carrier is reflected in such a way that essentially no excitation radiation reaches the detection beam path. However, Thorwirth does not teach how to adapt the disclosed arrangement to enable depth sectioned fluorescence imaging in a turbid medium.

SUMMARY OF THE INVENTION

An object of the present invention is to provide an apparatus and method for enabling analytical imaging of an object.

Another object of the present invention is to provide an improvement in such an apparatus and method for enabling depth sectioned fluorescence imaging in a turbid medium, such as human or animal tissue, in such a manner as to substantially minimize the excitation radiation from reaching the detection beam path. Minimizing the excitation radiation that reaches the detection beam path both minimizes the potential for that excitation radiation to cause background in the fluorescence signal, and enables low cost emission filtration with high transmission.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the claims.

According to one aspect of the present invention, there is provided an imaging system for imaging an object. More specifically, there is provided an improvement in an imaging system enabling depth sectioned fluorescence imaging in a turbid medium, such as human or animal tissue, in such a manner as to substantially minimize the excitation radiation from reaching the detection beam path. The imaging system includes an arrangement of the excitation radiation source such that the optical axis of the source is inclined relative to the optical axis of the camera, the optical plane of the source and the optical plane of the object are subject to a Scheimpflug condition provided by projection optics, and the angle of inclination of the source is selected such that the component of the excitation radiation incident upon the object that is not absorbed by the object is scattered in such a way that substantially minimizes excitation radiation from reaching the detection beam path.

One embodiment of the invention concerns an apparatus for quantitative modulated fluorescence imaging to perform depth sectioned fluorescence imaging of a turbid sample including a fluorescent turbid medium. The apparatus includes projection optics, including a first optical axis, to expose the turbid sample to a periodic pattern of excitation radiation to provide depth-resolved discrimination of fluorescent structures within the turbid medium; an image capture module, including a second optical axis and a detection beam path, to receive a data image from the sample; and a signal processor to transform the data image from the sample, spatially filter the transformed data image from the sample, and reconstruct the filtered, transformed data image from the sample. The embodiment includes an arrangement whereby the first optical axis is inclined relative to the second optical axis; the projection optics include an object plane and an image plane that are subject to a Scheimpflug condition; and the projection optics has an angle of inclination relative to an image plane of the apparatus, the angle of inclination being selected such that the component of excitation radiation incident upon the sample that is not absorbed by the sample is scattered in such a way that substantially reduces excitation radiation from reaching the detection beam path. In another embodiment, the periodic pattern of excitation radiation has periodicity in a direction perpendicular to a direction of a projection of the first optical axis onto the image plane, so that the phase of the periodic pattern of excitation radiation does not change with increasing depth into an image space.

One embodiment of a method according to the invention concerns quantitative modulated fluorescence imaging to perform depth sectioned fluorescence imaging of a turbid sample composed of a fluorescent turbid medium. The method comprises using a computer to perform steps of: acquiring two or more fluorescence image sets from two or more sets of projection optics, whose optical axes have different angles of inclination relative to an optical axis of an image capture module, to provide coverage of regions shadowed, by sample topography, for any one set of projection optics; and merging the two or more fluorescence image sets.

Another embodiment of a method according to the invention also concerns a method for performing depth sectioned fluorescence imaging of a turbid sample including a fluorescent turbid medium. The method uses an apparatus for quantitative modulated fluorescence imaging, the apparatus including projection optics with a first optical axis, to expose the turbid sample to a periodic pattern of excitation radiation to provide depth-resolved discrimination of fluorescent structures within the turbid medium; an image capture module, including a second optical axis and a detection beam path, to receive a data image from the sample; and a signal processor to transform the data image from the sample, spatially filter the transformed data image from the sample, and reconstruct the filtered, transformed data image from the sample. The method includes steps of: inclining the first optical axis relative to the second optical axis; providing in the projection optics an object plane and an image plane that are subject to a Scheimpflug condition; and inclining the projection optics at an angle of inclination relative to an image plane of the apparatus, the angle of inclination being selected such that the component of excitation radiation incident upon the sample that is not absorbed by the sample is scattered in such a way that substantially reduces excitation radiation from reaching the detection beam path. In another embodiment of the method, a further step comprises providing the periodic pattern of excitation radiation with a periodicity in a direction perpendicular to a direction of the projection of the first optical axis onto the image plane, so that the phase of the periodic pattern of excitation radiation does not change with increasing depth into an image space.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIGS. 7A, 7B and 7C show cutaway diagrammatic views of the image capture module configured according to FIG. 2.

FIG. 8 shows diagrammatic views of the spatially modulated excitation radiation of FIGS. 7A, 7B and 7C.

FIG. 17 shows a cutaway perspective view of components of the image capture module of the imaging system of FIG. 1 in accordance with a third embodiment of the present invention wherein spatially modulated excitation radiation is delivered from direction "a" using a doubly telecentric Scheimpflug lens system.

FIG. 19 shows a summarized comparison of the depth-of-modulation response from the optical simulation results of FIGS. 9 and 18.

DETAILED DESCRIPTION OF THE INVENTION

Figure 1:
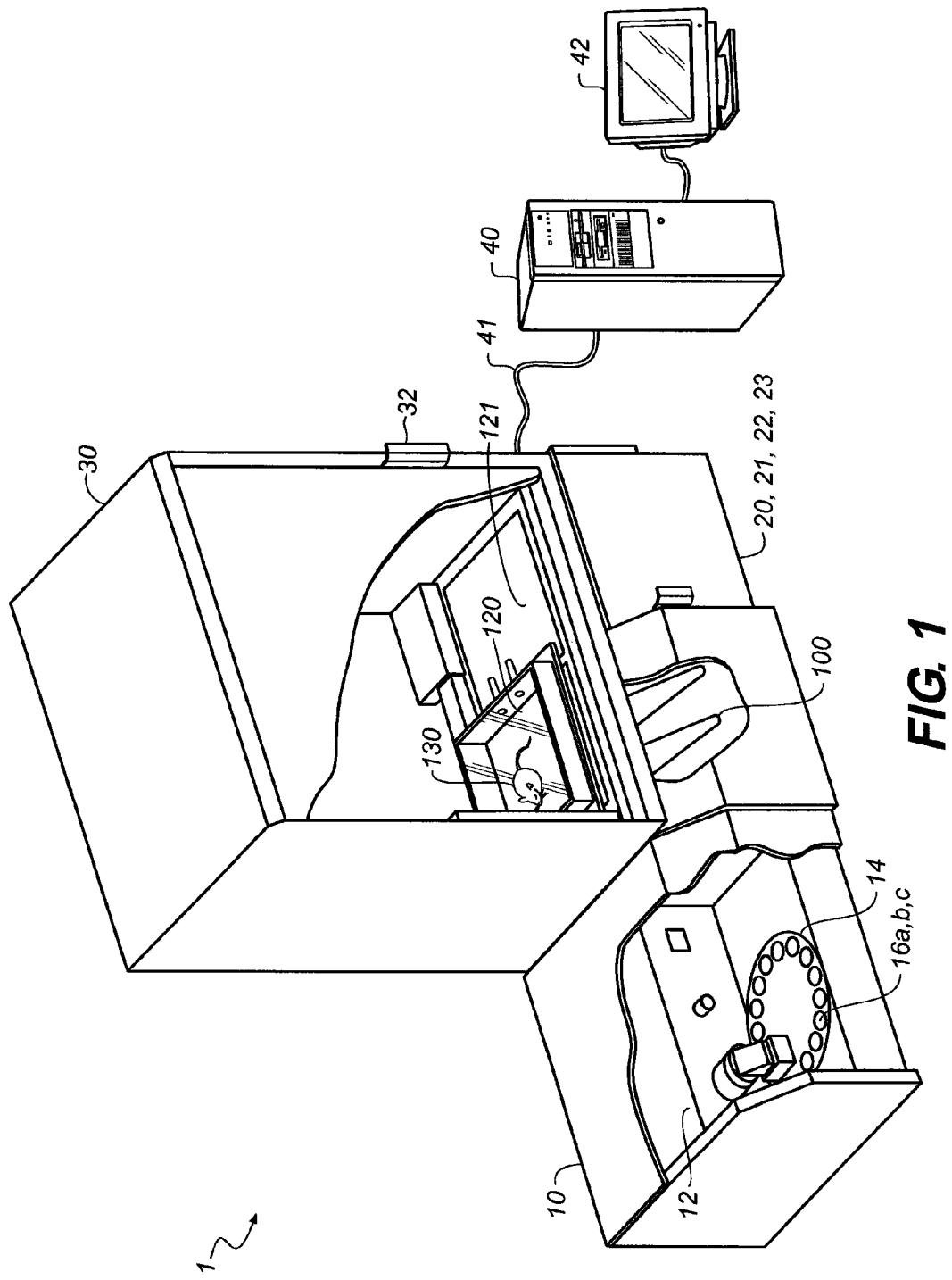
FIG. 1 shows a partially cutaway perspective view of an exemplary electronic imaging system.

The invention has been described in detail with particular reference to certain preferred embodiments thereof, but it will be understood that variations and modifications can be effected within the spirit and scope of the invention. The following is a detailed description of the preferred embodiments of the invention, reference being made to the drawings in which the same reference numerals identify the same elements of structure in each of the several figures.

FIG. 1 shows a partially cutaway perspective view of an exemplary electronic imaging system 1. The imaging system includes an excitation radiation source 10 for fluorescence excitation, an image capture module 20 to receive the data image from a sample, a sample cabinet 30, and a communication and computer control system 40. Source 10 includes a lamp unit 12, for example a halogen or xenon lamp unit, and an excitation filter wheel 14 containing a plurality of excitation filters 16a, b, and c. Alternative excitation radiation sources known in the art include lamp sources employing an excitation filter slider, light emitting diode based sources, and laser sources. Source 10 is optically coupled to image capture module 20, for example by a randomized fiber optic bundle, not illustrated. Image capture module 20 delivers excitation radiation 100 via projection optics to an optically transparent platen 120, which is incorporated into a subject stage 121, and upon which is placed an immobilized subject, such as an anesthetized mouse 130. Aside from the excitation radiation 100, image capture module 20 is substantially optically sealed from ambient light. Sample cabinet 30 is also substantially optically sealed from ambient light, and includes a door 32. Communication and computer control system 40 communicates with image capture module 20 via a communication cable 41, and can include a display device 42, for example, a computer monitor.

Figure 2:
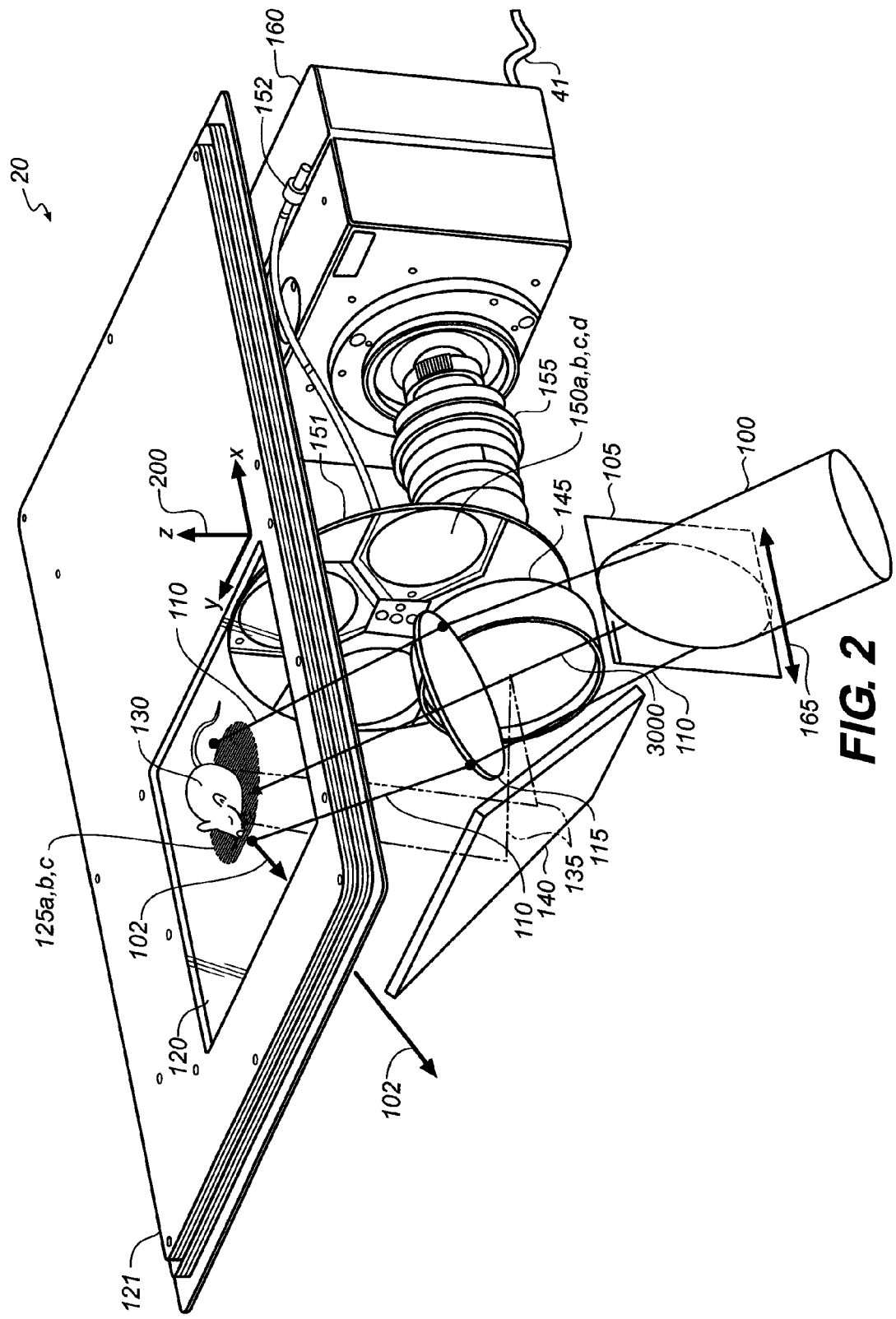
FIG. 2 shows a cutaway perspective view of components of the image capture module of the imaging system of FIG. 1 in accordance with a first embodiment of the present invention wherein spatially modulated excitation radiation is delivered from direction "a" using a non-telecentric Scheimpflug lens system.

FIG. 2 shows a cutaway perspective view of components of image capture module 20 in accordance with a first embodiment of the present invention wherein spatially modulated excitation radiation is delivered from direction "a" using projection optics comprised of a non-telecentric Scheimpflug lens system 115. The X-Y-Z coordinate system is defined 200. Excitation radiation 100 is transmitted through a one-dimensional spatial modulation grid 105. The spatial modulation grid is coplanar with the object plane of a non-telecentric Scheimpflug lens system 115. In the embodiment shown, the non-telecentric Scheimpflug lens system includes a single lens group as indicated; however, generally more than one lens group may comprise a non-telecentric Scheimpflug lens system. The spatial modulation grid is configurable or movable to produce a plurality of phases that shift along the direction indicated by arrow 165. Lens system 115 delivers the spatially modulated excitation radiation through a beam path 110 to the top surface of the platen 120, which surface is coplanar with the image plane of lens system 115, i.e., the X-Y plane. By definition, a Scheimpflug lens system forms an image of an object whereby the object and image planes are not parallel to each other, but are instead inclined with respect to each other. The examples used throughout this specification show object and image planes (such as at grid 105 and top surface of platen 120, respectively) that are perpendicular with respect to each other; but in general the inclination of the object and image planes can be any arbitrary angle, including obtuse angles if folding mirrors are used in the Scheimpflug lens system. Upon reaching the platen surface, the spatially modulated excitation radiation 125a, b, and c, propagates further into the space beyond the platen, i.e., into the image space depth, which is the positive Z direction. The characteristics of the spatial profile of the excitation radiation, such as the depth of modulation and DC level at various planes parallel to the X-Y image plane through the image space depth, depend on both the image forming properties of the lens system, such as the depth of focus, as well as the optical properties, such as the turbidity, of the medium in the image space. An immobilized subject, such as a fluorophore-labeled anesthetized mouse 130, situated at the platen surface fills the image space with a turbid medium and provides a spatially distributed fluorescence signal with spatial modulation in proportion to the spatially modulated excitation radiation through the image space. The image space of the excitation Scheimpflug lens system 115 is the object space of the fluorescence detection lens system. The fluorescence signal is imaged through a beam path 135 by a detection lens system including a detection lens 155 and a detection lens diopter 145, onto a sensor in a digital camera 160, such as a thermoelectrically cooled charge coupled device camera. A folding mirror 140 inserted in the detection beam path enables a compact layout of the image capture module. A plurality of emission filters 150a, b, c, and d in an emission filter wheel 151 provides spectral selection of the fluorescence signal using an actuator 152, as well as rejection of excitation radiation from the sensor. The component of the excitation radiation from beam path 110 that is not absorbed by the mouse 130 on platen 120 is scattered predominantly along a direction indicated by the arrow 102; so that the excitation radiation is scattered away from the detection beam path, thereby minimizing the potential for that excitation radiation to cause background in the fluorescence signal. Furthermore, because cost of the emission filters is increased and fluorescence transmission of the emission filters is decreased with increased rejection of the excitation radiation, the reflection of the excitation radiation away from the detection beam path enables low cost emission filtration with high transmission.

Figure 3:
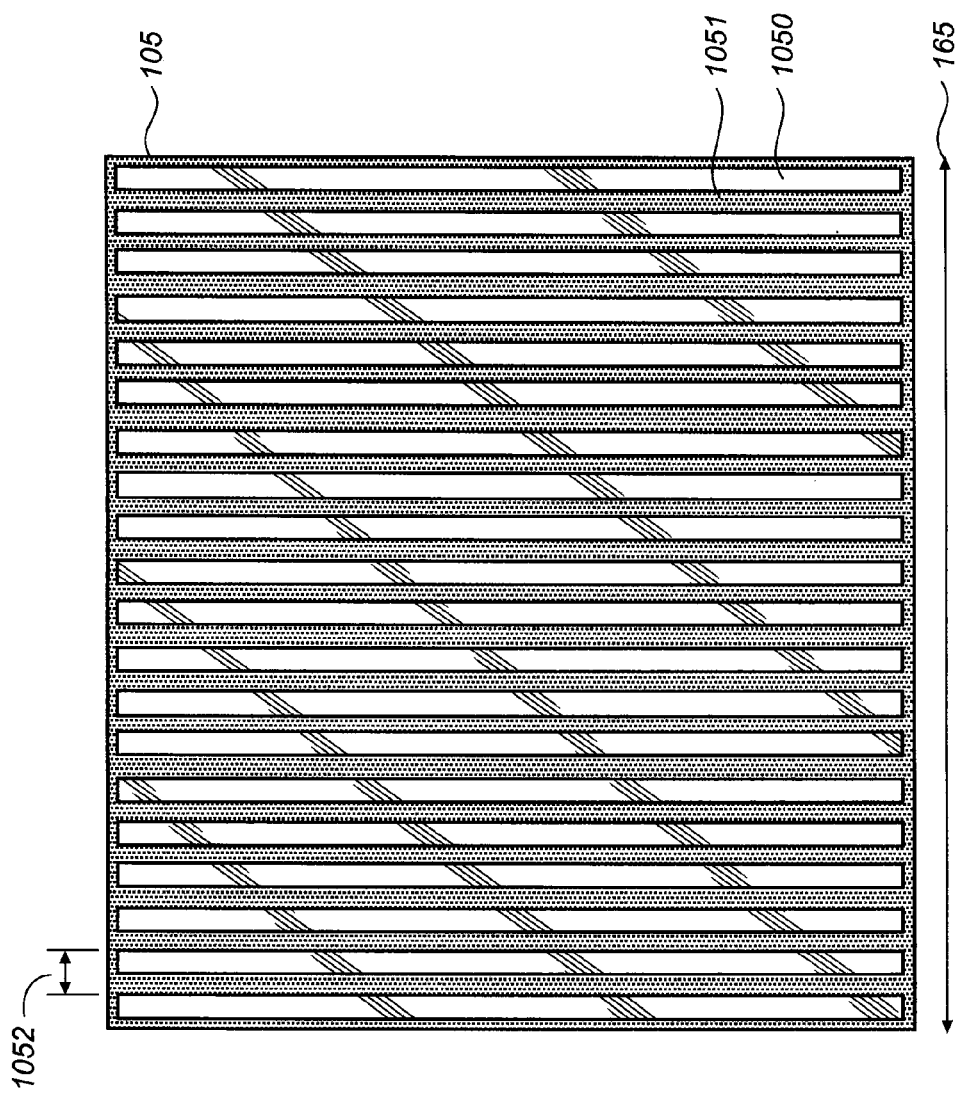
FIG. 3 shows a diagrammatic view of the spatial modulation grid used in the image capture module of FIG. 2.

FIG. 3 shows a diagrammatic view of spatial modulation grid 105 used in image capture module 20. In the embodiments described throughout, the spatial modulation grid includes an alternating periodic pattern of transparent and non-transparent stripes, 1050 and 1051, respectively. The spatial modulation grid is oriented so that the alternation of the periodic pattern of transparent and non-transparent stripes is along the direction shown by arrow 165 in FIGS. 2 and 3, i.e., parallel to the image plane, in this example the platen surface. Furthermore, the spatial modulation grid can be incrementally shifted or translated along the direction indicated by the arrow 165, by fractions of the spatial modulation period 1052. Such translation can be used to produce a plurality of phases of the spatial modulation corresponding to a plurality of fluorescence images comprising a fluorescence image set, whereby one phase of spatial modulation is selected for each fluorescence image in the fluorescence image set so as to perform depth sectioning. The translation of the spatial modulation grid may be achieved by a piezo-electronically driven actuator, not illustrated, wherein amplified voltage is applied to a piezoelectric crystal to change its length, thereby providing highly accurate repositioning of the grid pattern.

Figure 4:
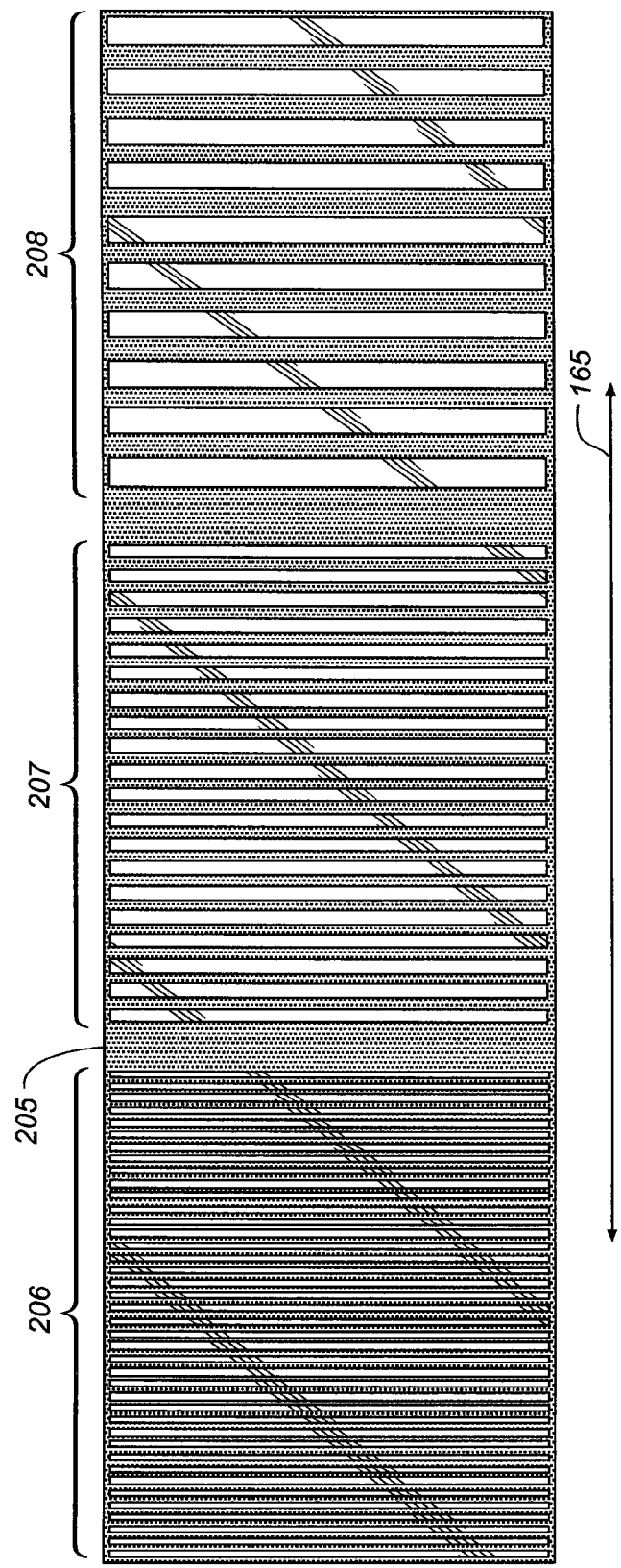
FIG. 4 shows a diagrammatic view of a plurality of spatial modulation grids, each with a different spatial frequency, formed in series in a slider.

The spatial modulation grid 105 may be formed by selective removal of material from a solid sheet of material, and may be simply a single grid with a given spatial modulation frequency. Alternatively, as shown in FIG. 4, grids may be formed in, and selected by means of, a slider 205 including a plurality of spatial modulation grids, each with a different spatial frequency, for example "high" 206, "medium" 207, and "low" 208, in series. The different spatial frequencies enable different resolutions of depth sectioning. The series of spatial modulation grids may be distributed along the direction indicated by the arrow 165 to be in the same direction as the direction of spatial modulation phase shift, thereby simplifying the actuation means necessary to achieve both spatial modulation phase shift as well as grid selection. Alternatively, the series of spatial modulation grids may be distributed along a direction different from the direction of spatial modulation phase shift. In alternative embodiments, the spatial modulation grid may be an electronically programmable electro-optic matrix, for example a liquid crystal matrix or a digital micromirror matrix.

Figure 5:
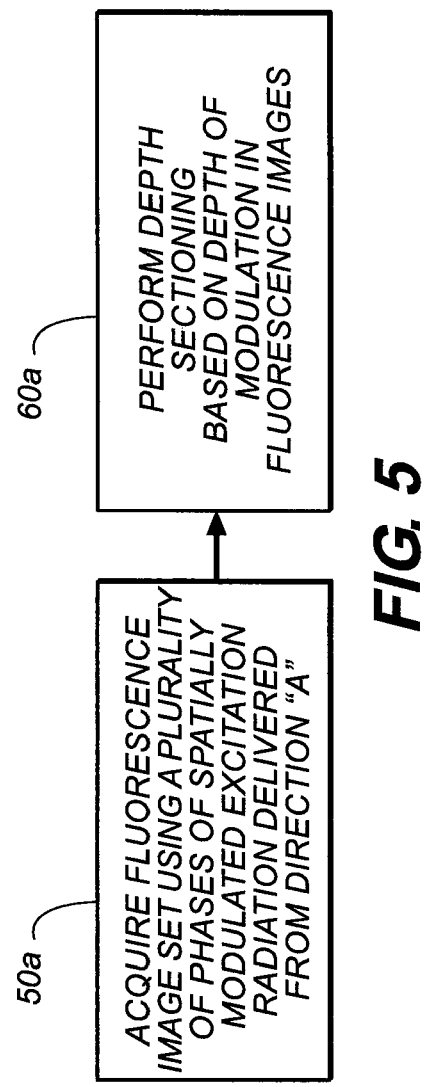
FIG. 5 shows a workflow diagram in accordance with a first method of the present invention.

FIG. 5 shows a workflow diagram in accordance with a first method of the present invention. First, a fluorescence image set is acquired using a plurality of phases of spatially modulated excitation radiation delivered from direction "a", step 50a. Second, depth sectioning is performed based on the depth of modulation in the fluorescence images, step 60a. The depth sectioning is performed by communication and computer control system 40 which includes a signal processor to Fourier transform the data image of the sample, spatially filter the transformed data image of the sample, and reconstruct the filtered, transformed data image of the sample.

Figure 6:
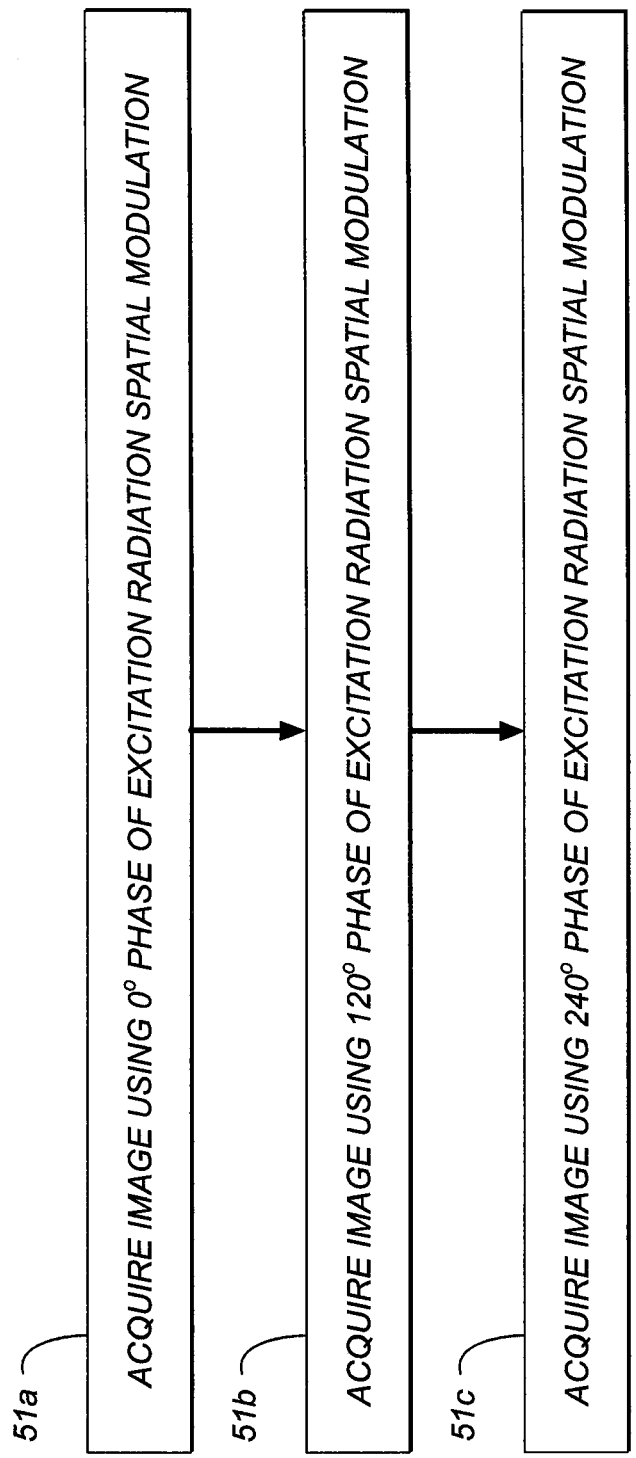
FIG. 6 shows a workflow diagram of an exemplary method used in step 50a of FIG. 5.
Figure 9A:
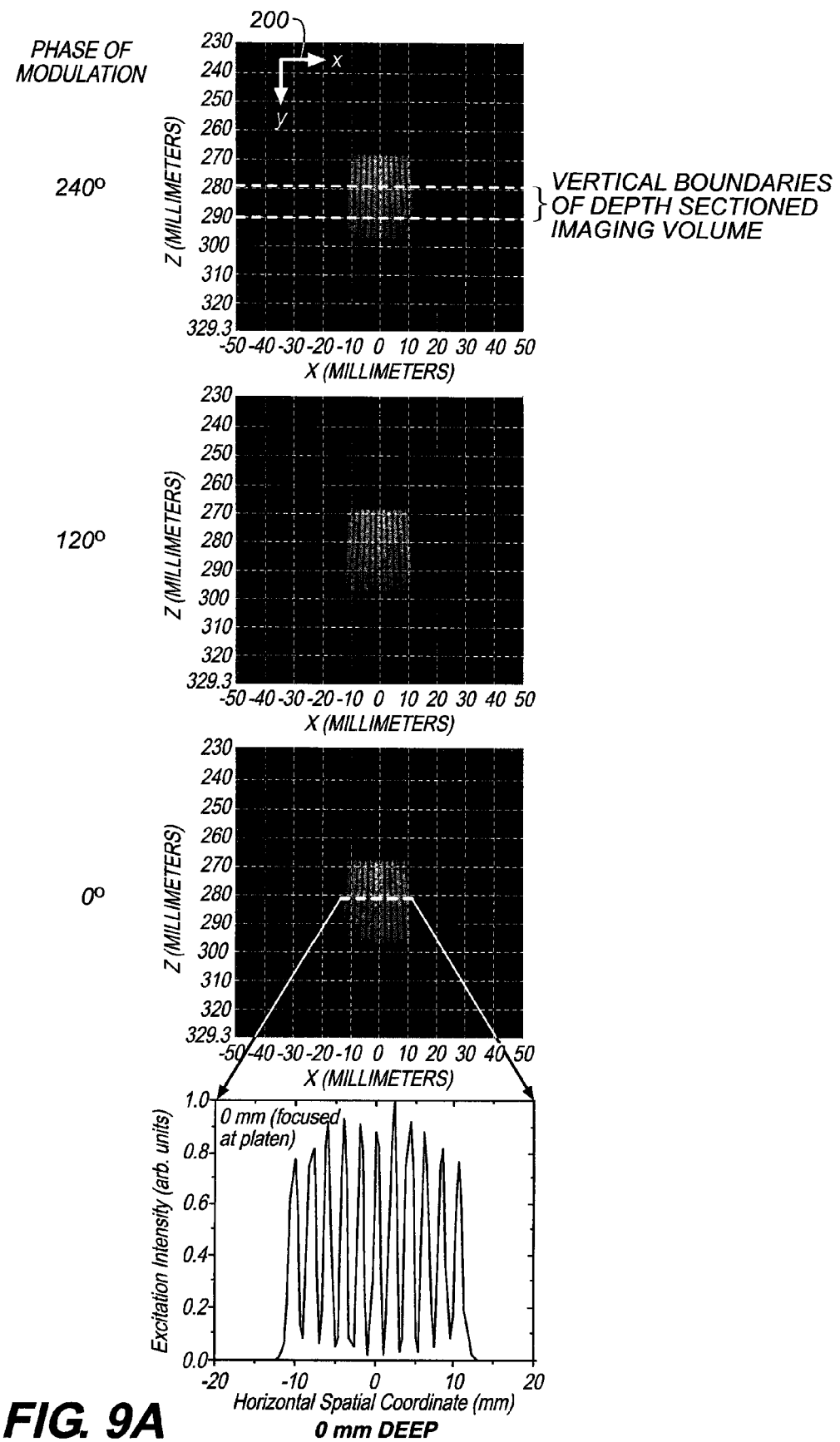
FIG. 9 shows optical simulation results generally representing the embodiment diagrammatically shown in FIG. 2.
Figure 9B:
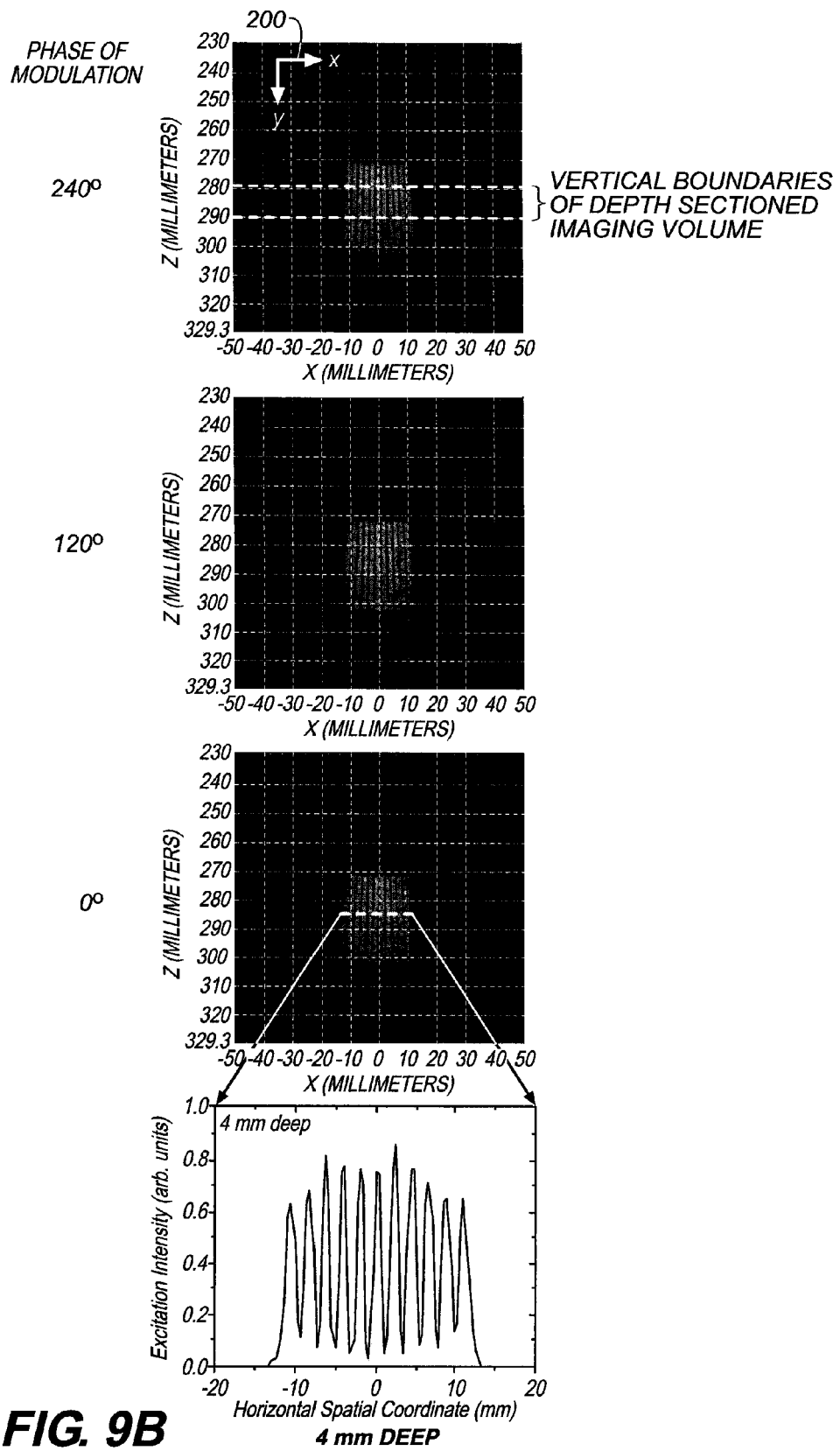
Figure 9C:
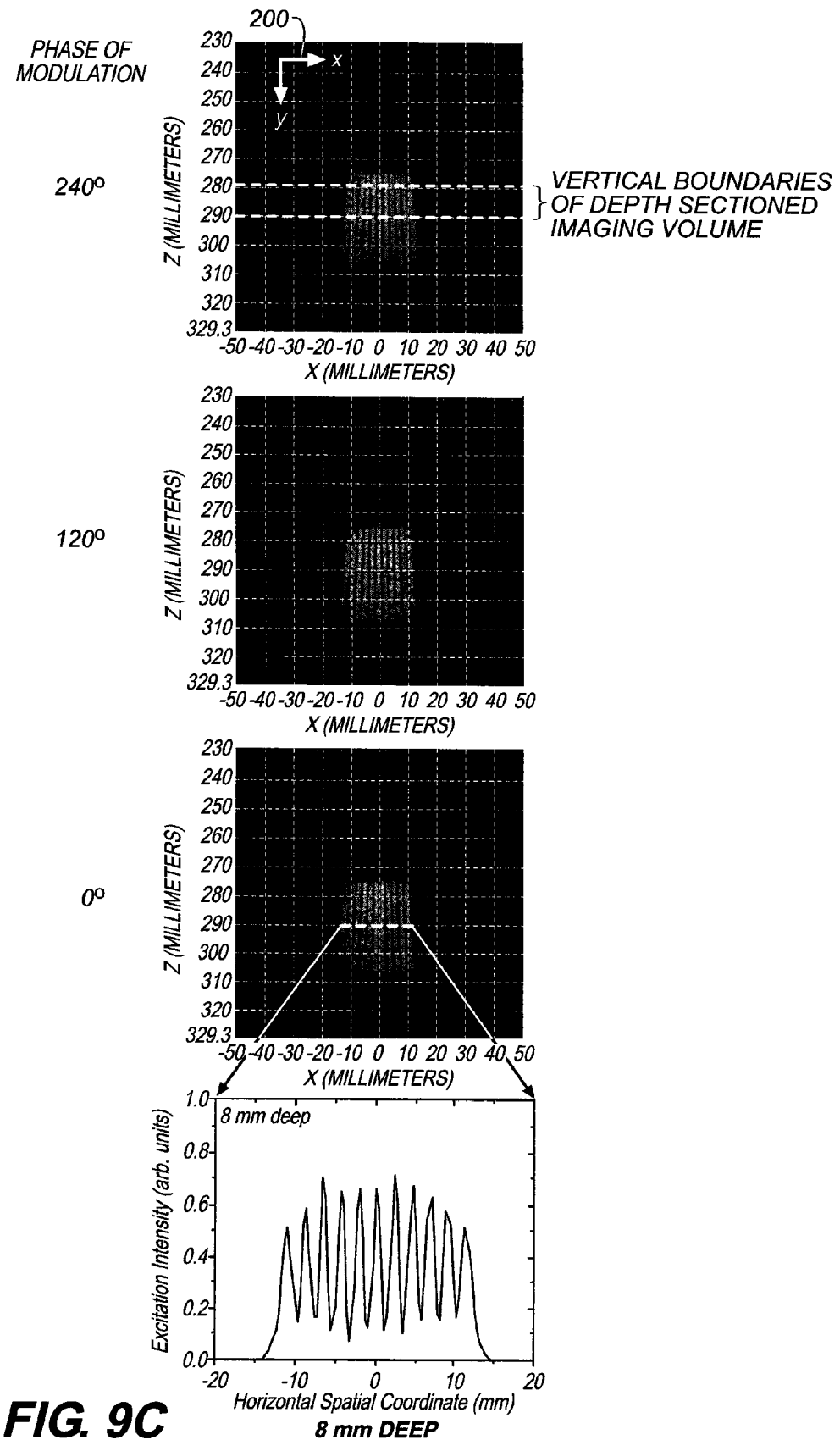
Figure 9D:
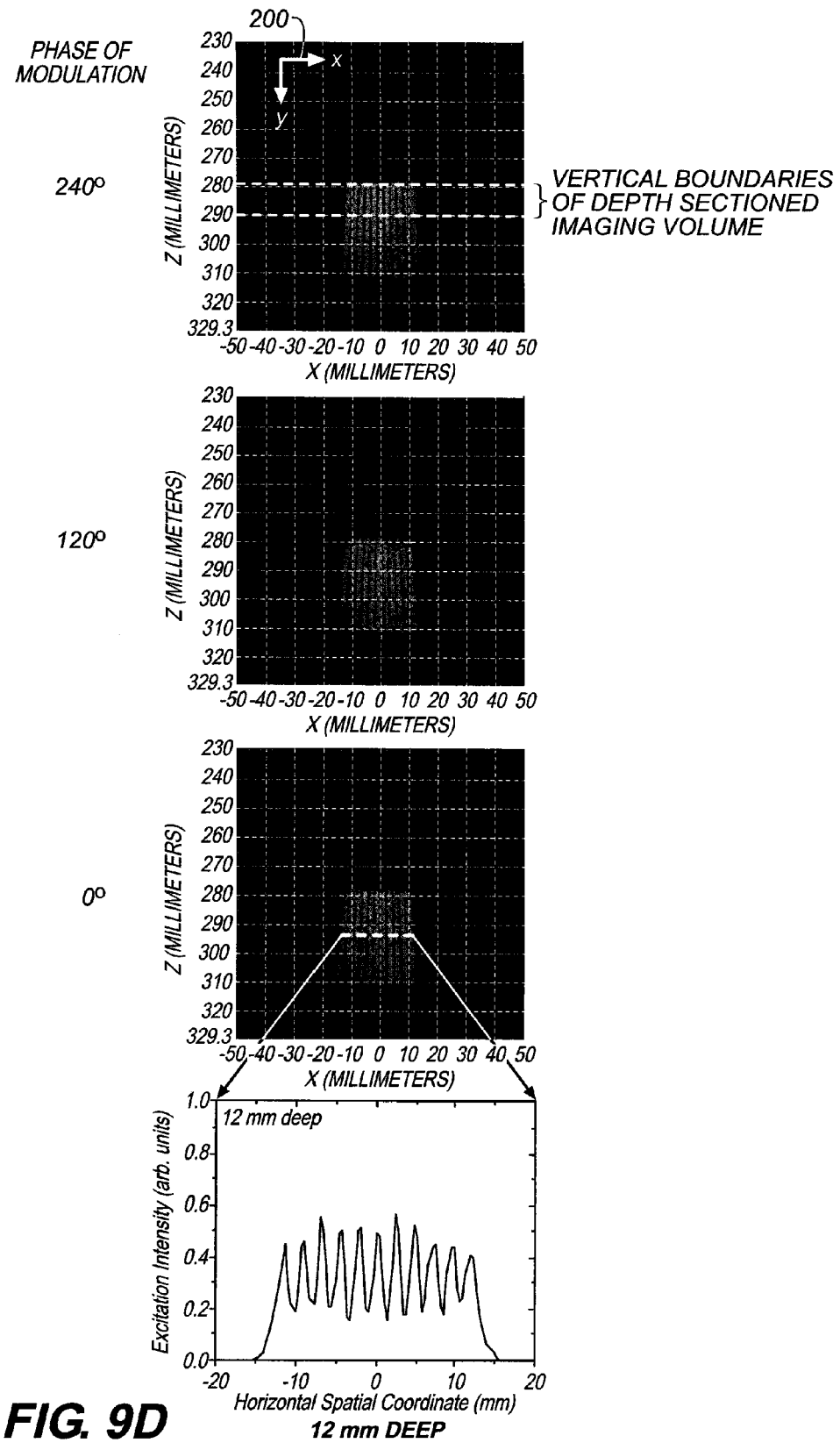
Figure 9E:
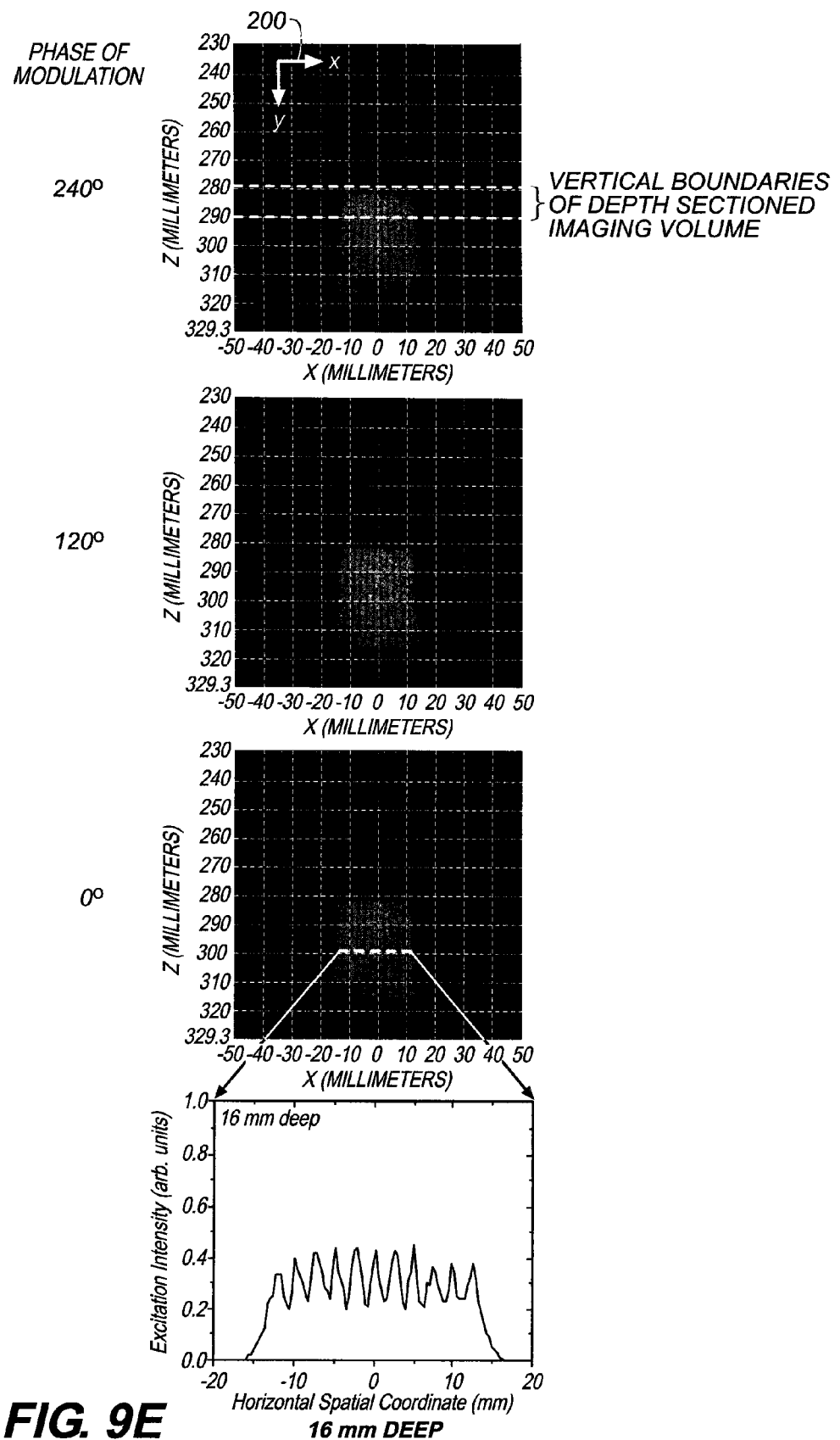

FIG. 6 shows a workflow diagram of an exemplary method used in step 50a of FIG. 5 wherein the plurality of phases includes three relative phases, specifically 0 degrees step 51a, 120 degrees step 51b, and 240 degrees step 51c, i.e., one-third steps of the spatial modulation period length. FIGS. 7A, 7B and 7C show cutaway diagrammatic views of image capture module 20. The perspective of the view is from directly below platen 120. FIGS. 7A, 7B and 7C show the spatially modulated excitation radiation 125a, b, and c, respectively, whereby the relative phase of the spatial modulation is 0 degrees, 120 degrees, and 240 degrees, respectively. X-Y-Z coordinate system 200 is shown. FIG. 8 shows diagrammatic views of the spatially modulated excitation radiation of FIGS. 7A, 7B and 7C in the X-Y plane. The relative phase is shifted by 0 degrees, 120 degrees, and 240 degrees in 125a, b, and c, respectively.

FIG. 9 shows optical simulation results generally representing the embodiment diagrammatically shown in FIG. 2. The optical simulation was executed using the TracePro® optical modeling software from Lambda Research Corporation (www.lambdares.com). A spatial modulation grid pitch of 2 mm, a biconvex lens with focal length 103 mm as the non-telecentric Scheimpflug lens system, an object plane-to-lens distance of 194 mm, and an image plane-to-lens distance of 194 mm, were used in the simulation. The optical simulation results include the spatially modulated excitation radiation patterns present at a series of planes, parallel to the X-Y image plane, distributed through the image space depth beyond the platen, i.e., in the positive Z direction. See the first five plots at the bottom of FIG. 9 for depths of 0, 4, 8, 12 and 16 mm. Three different spatial modulation phases are shown for each depth. See the three rows of plots for modulation phases of 0, 120 and 240 degrees. Whereas the diagrams of the spatially modulated excitation radiation patterns 125a, b, and c of FIGS. 7A, 7B and 7C show an undersized round excitation radiation beam intersecting the spatial modulation grid, the optical simulations were performed using an excitation radiation beam that fills the spatial modulation grid so as to more clearly illustrate the distortion inherent to a non-telecentric Scheimpflug lens system. Specifically, the transverse magnification exhibits a gradient in the Y direction, i.e., along the direction parallel to the direction of the projection of the excitation radiation propagation vector onto the X-Y image plane. The transverse magnification in the Y direction increases with increasing distance away from the object plane of the non-telecentric Scheimpflug lens system. Furthermore, the transverse magnification also exhibits a gradient along the Z direction, normal to the image plane; the transverse magnification increases with increasing distance away from the X-Y image plane of the non-telecentric Scheimpflug lens system. In these simulations, the best focus is at 0 mm, defined as the platen surface. The simulations show that the depth of modulation of the excitation radiation pattern decreases with increasing depth into the image space beyond the platen surface; i.e., the pattern is going out of focus. These simulations were performed for the case where the medium in the image space beyond the platen is not turbid; if the medium were instead turbid, then the turbidity would accelerate the decrease of the depth of modulation of the excitation radiation pattern with increasing depth into the image space beyond the platen surface. The profiles taken along the X direction, i.e., along the direction perpendicular to the direction of the projection of the excitation radiation propagation vector onto the image plane, further illustrate the decrease of the depth of modulation, defined as the ratio of the amplitude of the spatial oscillation, i.e., AC, to the average, i.e., DC, level, of the excitation radiation pattern with increasing depth into the image space beyond the platen surface. The profiles also illustrate the rapid decrease in the DC level of the excitation radiation pattern with increasing depth into the image space beyond the platen surface due to the increase of the transverse magnification with depth, i.e., the excitation radiation spreads out over a larger area. The simulations also show that the spatially modulated excitation radiation pattern shifts in the positive Y direction, away from the object plane of the non-telecentric Scheimpflug lens system, with increasing depth into the image space beyond the platen surface. This shifting behavior is inherent to any Scheimpflug lens system and is due to abnormality of the propagation vector of the excitation radiation with respect to the image plane. This shifting behavior restricts the orientation of the spatial modulation to be aligned with the X direction so that the phase of the spatial modulation does not change with increasing depth into the image space beyond the platen surface. This shifting behavior also restricts the field of view of depth sectioning to that between the maximum Y extent of the X-Y image plane and the minimum Y extent of the deepest plane (shown by example as 16 mm deep).

Figure 10:
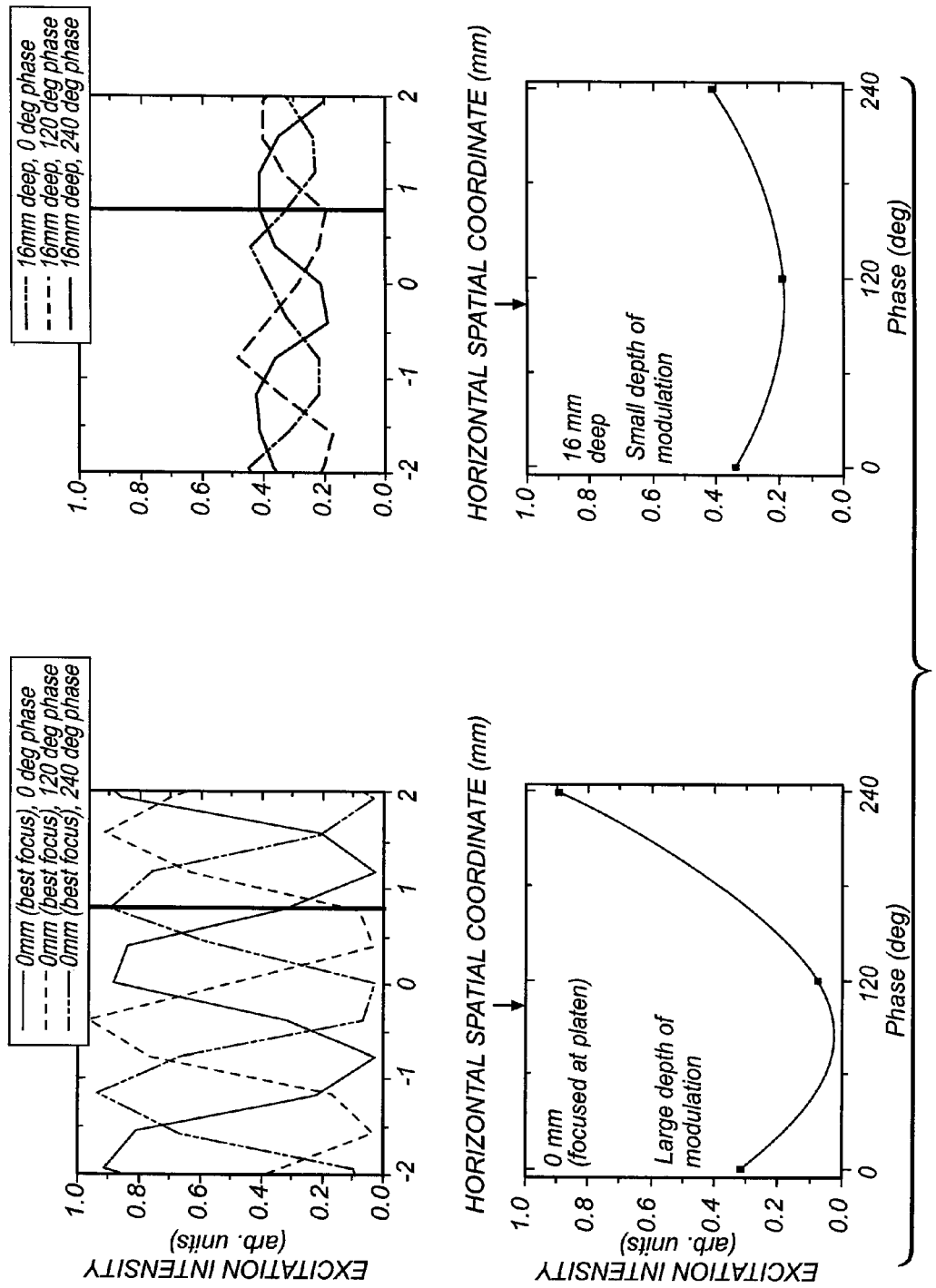
FIG. 10 shows detail of the optical simulation results from FIG. 9.

FIG. 10 shows four plots of detail of the optical simulation results from FIG. 9. The profiles show the excitation radiation spatial modulation, both at the image plane and at the plane 16 mm deep, in a 4 mm range around the center of the pattern. The profiles show the excitation radiation spatial modulation for the plurality of phases, by example three phases. The vertical bars in the profiles represent sampling points in the image plane and in the plane 16 mm deep. The plots of excitation intensity vs. phase, which are the intersection points of the vertical bars with the profiles corresponding to the three phases, show that at the sampling points, the depth of modulation decreases with increasing depth into the image space beyond the platen surface. FIG. 10 illustrates use of an algorithm of a type familiar to those skilled in the art to execute step 60a, namely the point-by-point analysis of the depth of modulation to achieve point-by-point depth sectioning. For example, the algorithm disclosed by Tromberg would suffice.

Figure 11:
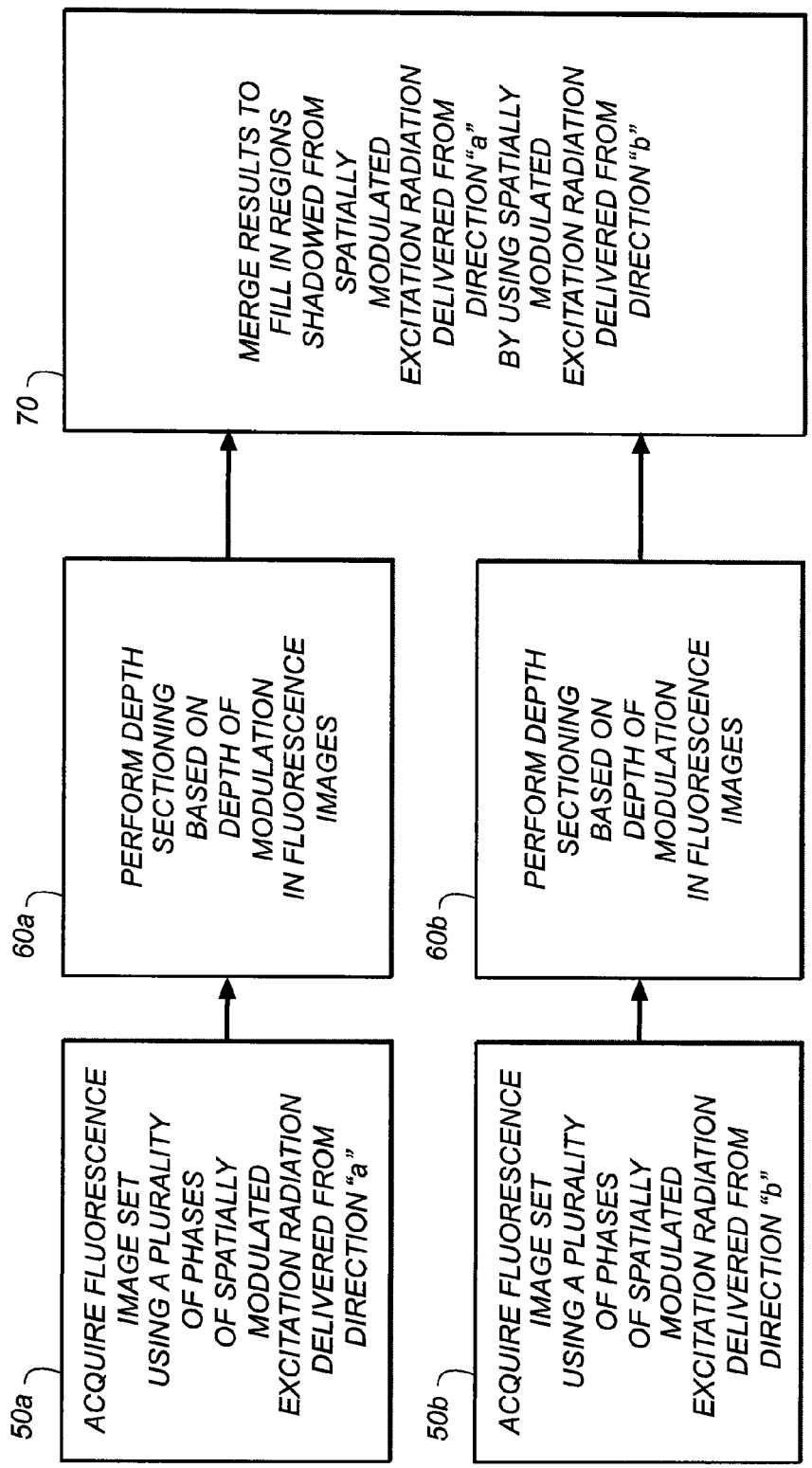
FIG. 11 shows a workflow diagram in accordance with a second method of the present invention.
Figure 12:
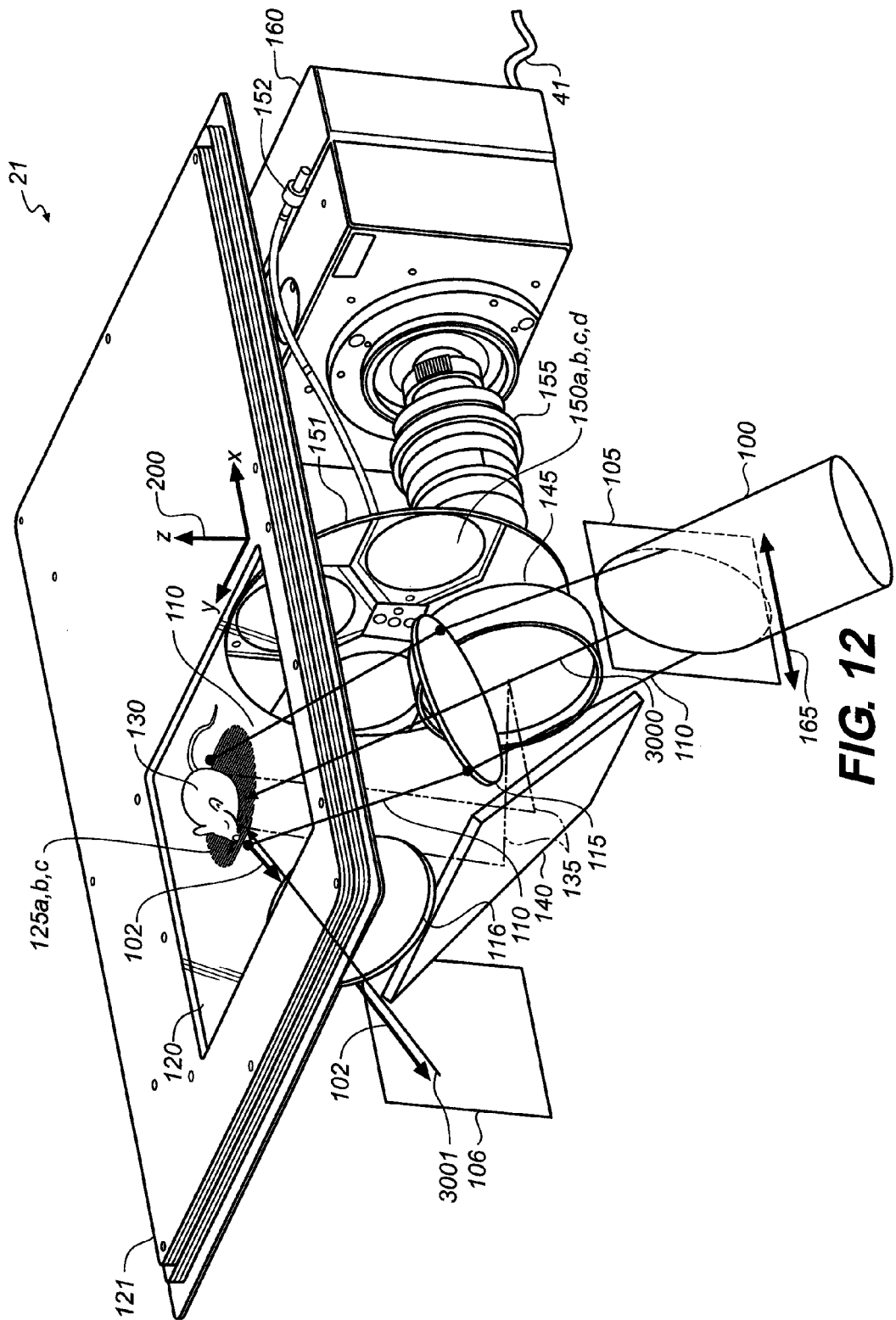
FIG. 12 shows a cutaway perspective view of components of the image capture module of the imaging system of FIG. 1 in accordance with a second embodiment of the present invention wherein spatially modulated excitation radiation is delivered from direction "a" using a non-telecentric Scheimpflug lens system.

FIG. 11 shows a workflow diagram in accordance with a second method of the present invention, as practiced using the capture module 21 of FIG. 12. First, a fluorescence image set is acquired using a plurality of phases of spatially modulated excitation radiation delivered from direction "a", step 50a. Second, depth sectioning is performed based on the depth of modulation in the fluorescence images, step 60a. Third, a fluorescence image set is acquired using a plurality of phases of spatially modulated excitation radiation delivered from direction "b", step 50b. Fourth, depth sectioning is performed based on the depth of modulation in the fluorescence images, step 60b. Last, the outputs of steps 60a and 60b are merged to fill in regions shadowed from spatially modulated excitation light delivered from direction "a" by using spatially modulated excitation light delivered from direction "b".

Figure 13:
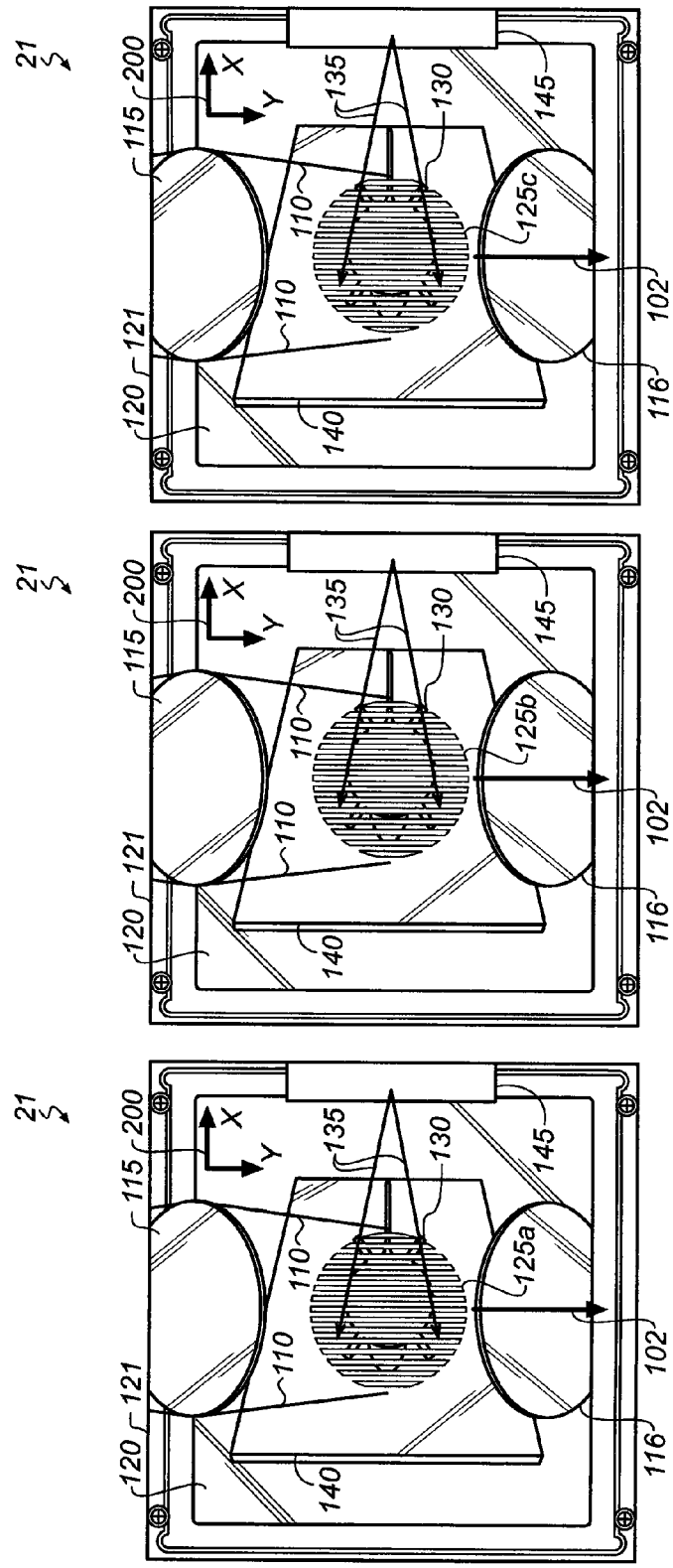
FIGS. 13A, 13B and 13C show cutaway diagrammatic views of the image capture module configured according to FIG. 12.

FIG. 12 shows a cutaway perspective view of components of the image capture module 21 in accordance with a second embodiment of the present invention wherein spatially modulated excitation radiation is delivered from direction "a" using projection optics including a non-telecentric Scheimpflug lens system 115. This embodiment is similar to the embodiment shown in FIG. 2, however an additional spatial modulation grid 106 and non-telecentric Scheimpflug lens system 116, mirror-symmetric to spatial modulation grid 105 and non-telecentric Scheimpflug lens system 115 across the X-Z plane bisecting the platen 120, are included for delivery of excitation radiation from direction "b" in an additional step. FIGS. 13A, 13B and 13C show cutaway diagrammatic views of the image capture module 21 configured according to FIG. 12. FIGS. 13A, 13B and 13C are similar to FIGS. 7A, 7B and 7C.

Figure 14:
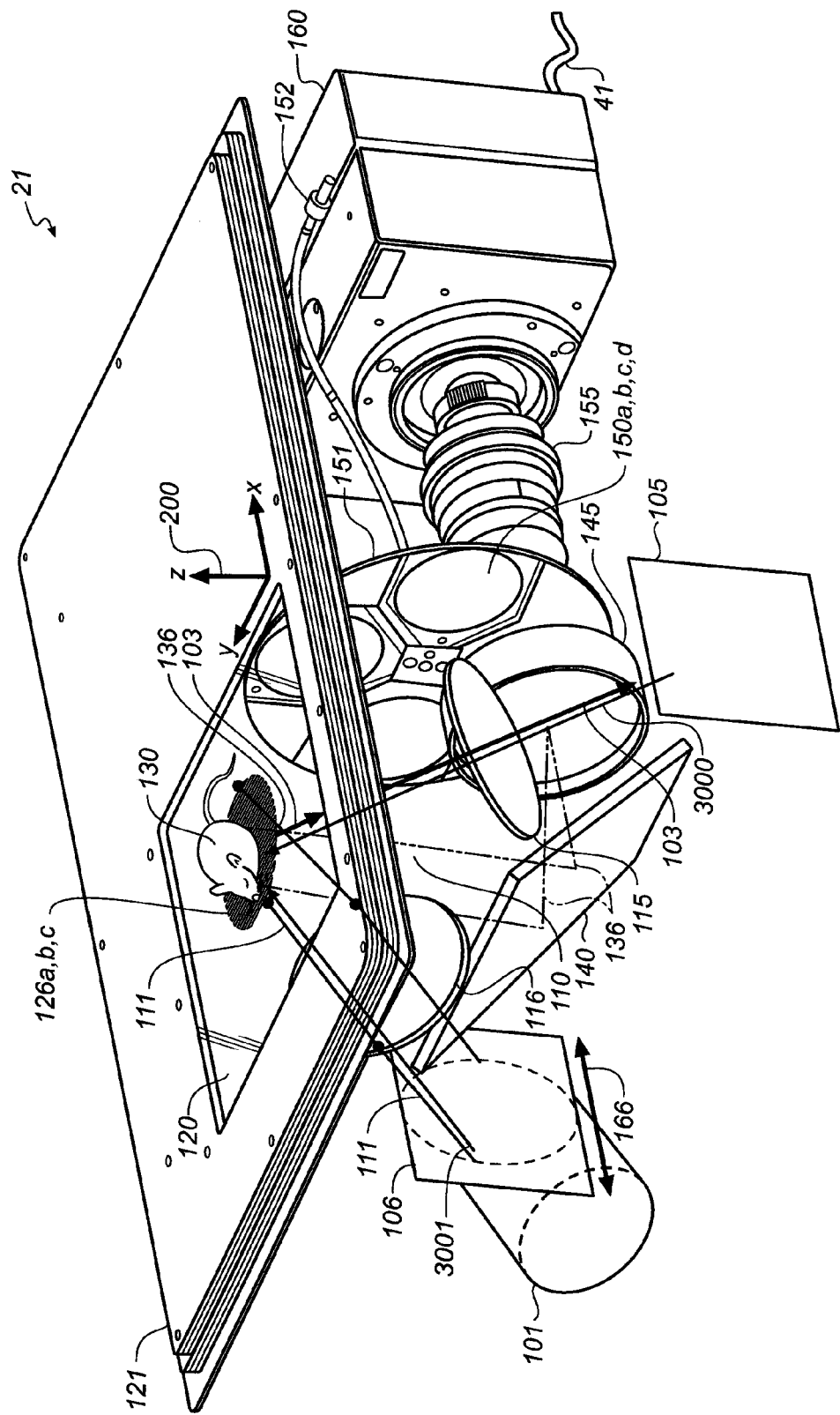
FIG. 14 shows a cutaway perspective view of the image capture module of FIG. 12 wherein spatially modulated excitation radiation is delivered from direction "b" using a non-telecentric Scheimpflug lens system.
Figure 15:
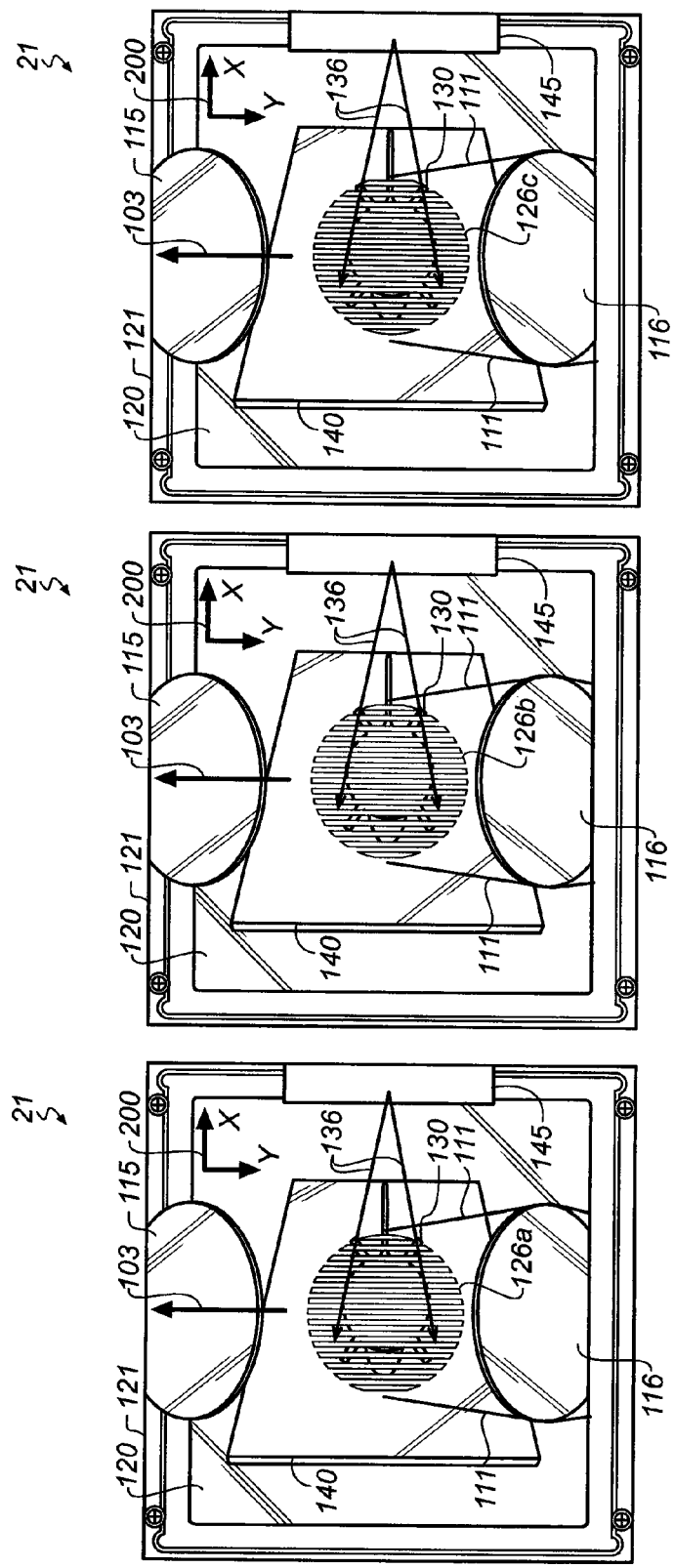
FIGS. 15A, 15B and 15C show cutaway diagrammatic views of the image capture module configured according to FIG. 14.

FIG. 14 shows a cutaway perspective view of the image capture module 21 of FIG. 12 wherein spatially modulated excitation radiation is delivered from direction "b" using projection optics including a non-telecentric Scheimpflug lens system 116. Excitation radiation 101 is transmitted through a one-dimensional spatial modulation grid 106. The spatial modulation grid is located at the object plane of a non-telecentric Scheimpflug lens system 116. The spatial modulation grid is configurable or movable to produce a plurality of phases that shift along the direction indicated by arrow 166. Lens system 116 delivers the spatially modulated excitation radiation through a beam path 111 to the surface of the platen 120 located at the image plane of the lens system, i.e., the X-Y plane. Upon reaching the platen surface, the spatially modulated excitation radiation 126a, b, and c, propagates further into the space beyond the platen, i.e., into the image space depth, which is the positive Z direction. The image space of excitation Scheimpflug lens system 116 is the object space of the fluorescence detection lens system. The fluorescence signal is imaged through a beam path 136 by the detection lens system described previously. The excitation radiation is reflected along a direction indicated by the arrow 103; therefore, the excitation radiation is reflected away from the detection beam path, thereby minimizing the potential for that excitation radiation to cause background in the fluorescence signal. FIGS. 15A, 15B and 15C show cutaway diagrammatic views of the image capture module 21 configured according to FIG. 14. FIGS. 15A, 15B and 15C are mirror-symmetric to FIGS. 13A, 13B and 13C across the X-Z plane bisecting the platen 120.

Figure 16:
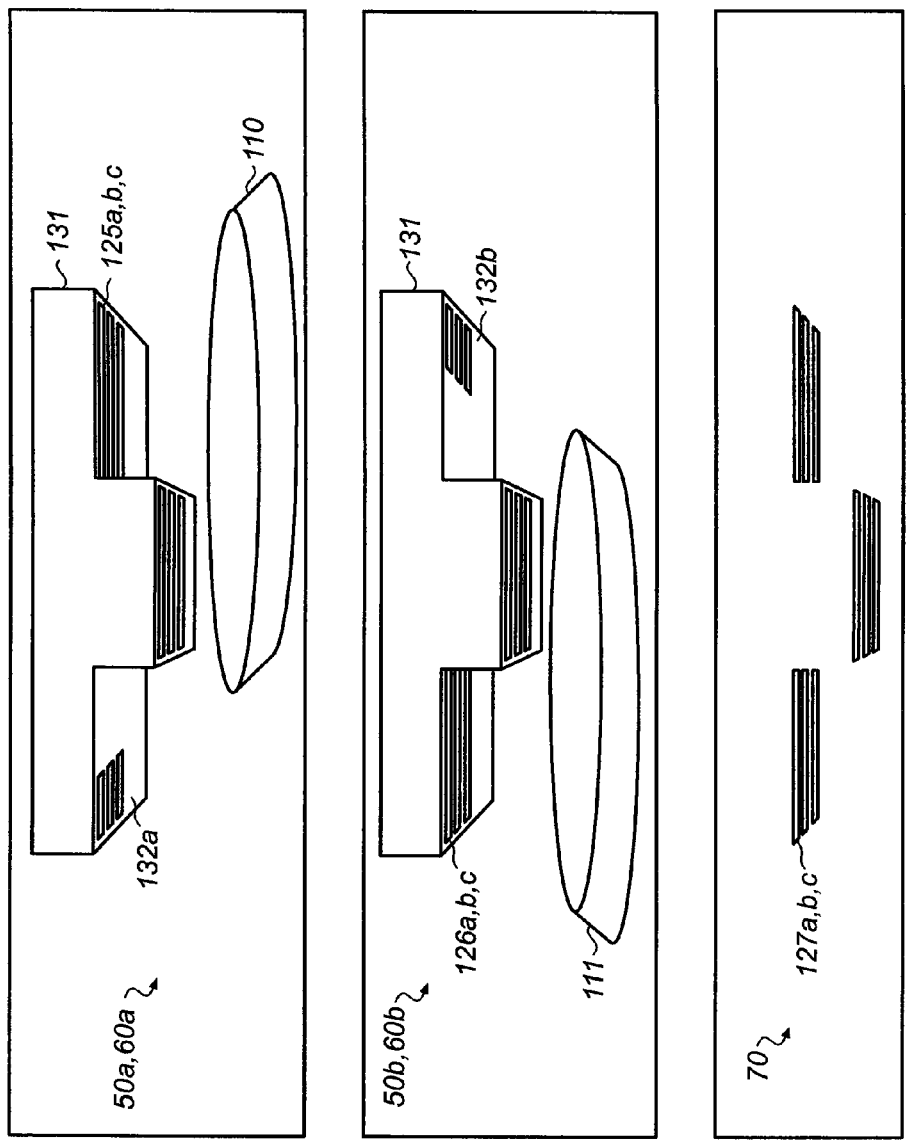
FIG. 16 shows a graphic representation of the workflow diagram of FIG. 11.
Figure 18A:
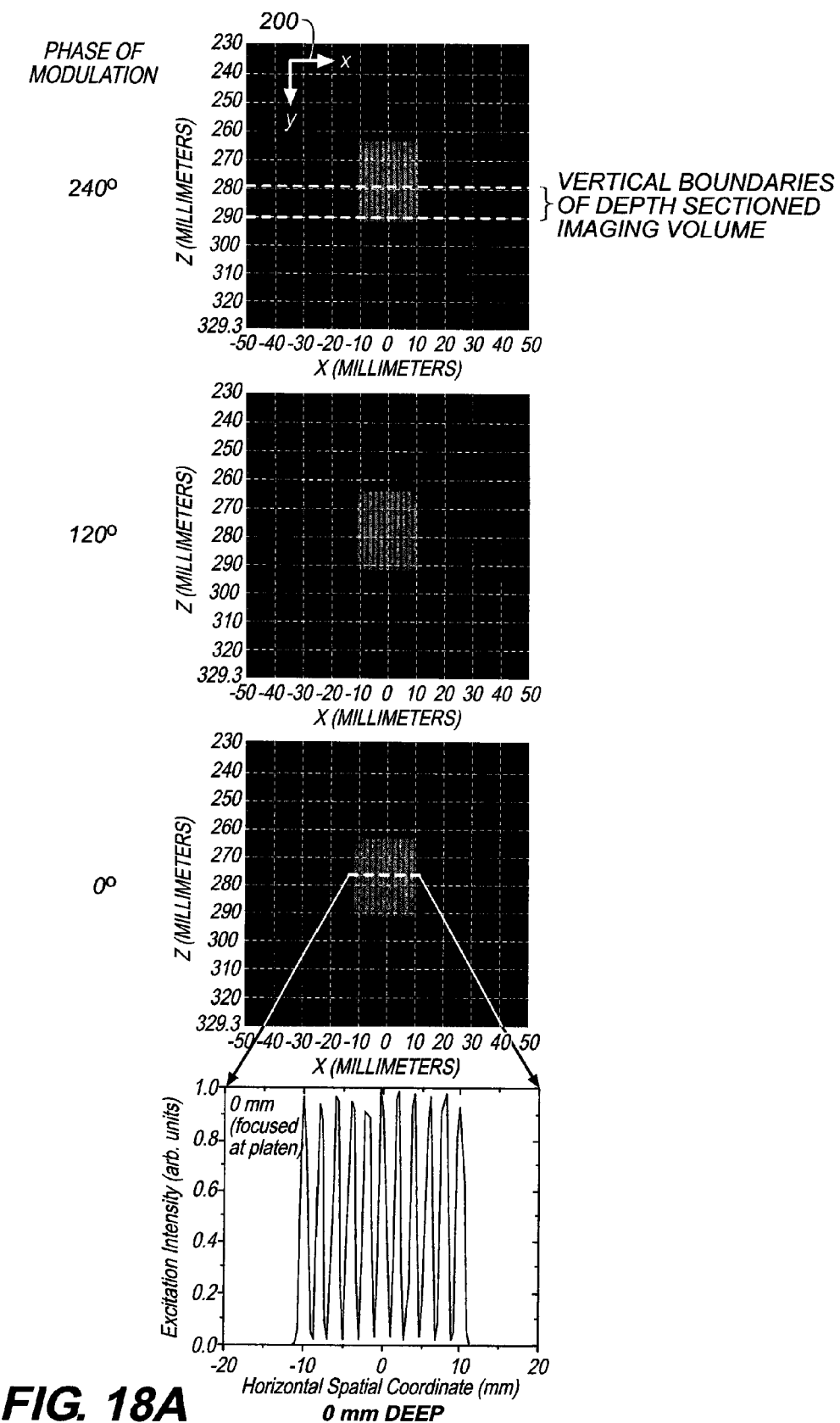
FIG. 18 shows optical simulation results generally representing the embodiment diagrammatically shown in FIG. 17.
Figure 18B:
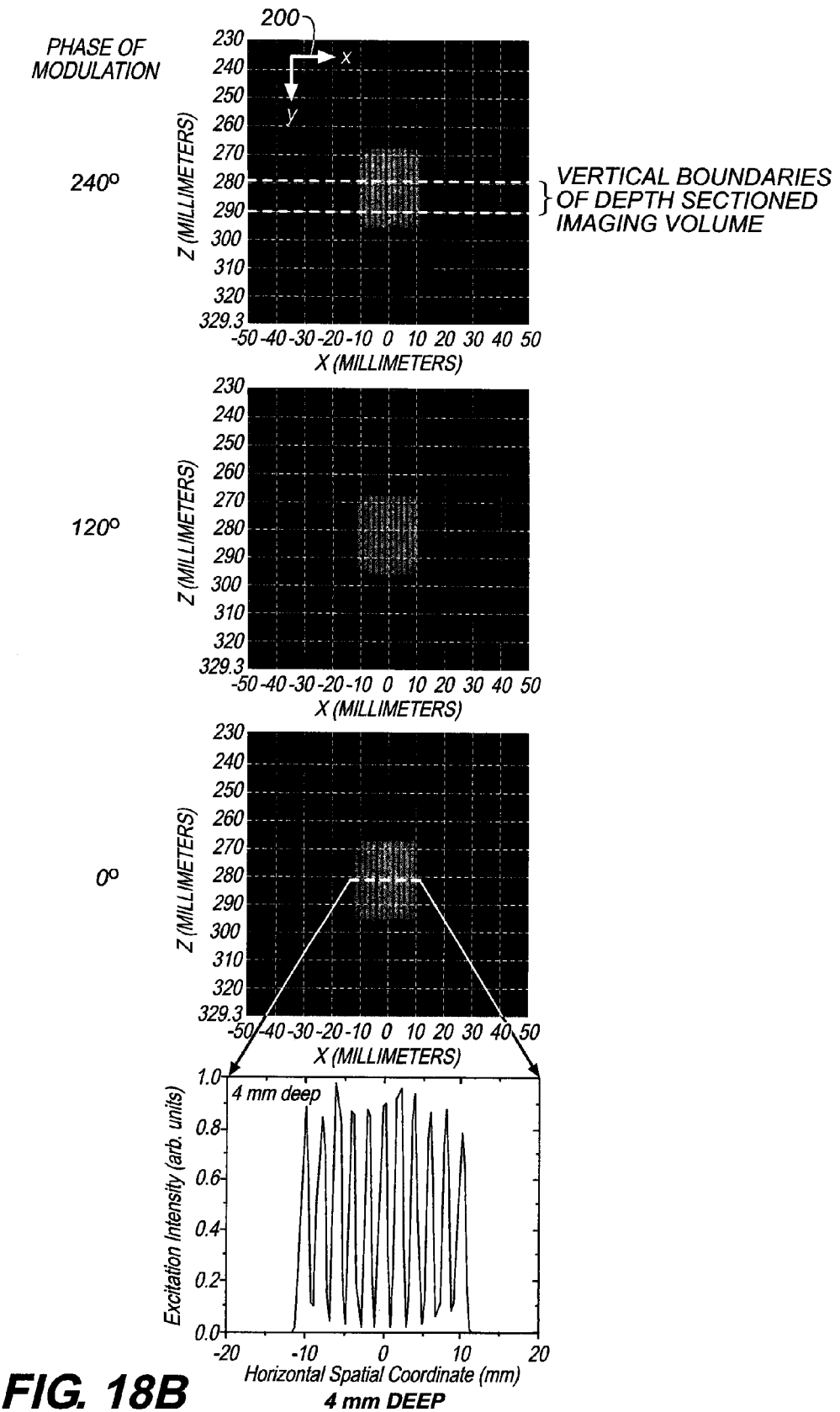
Figure 18C:
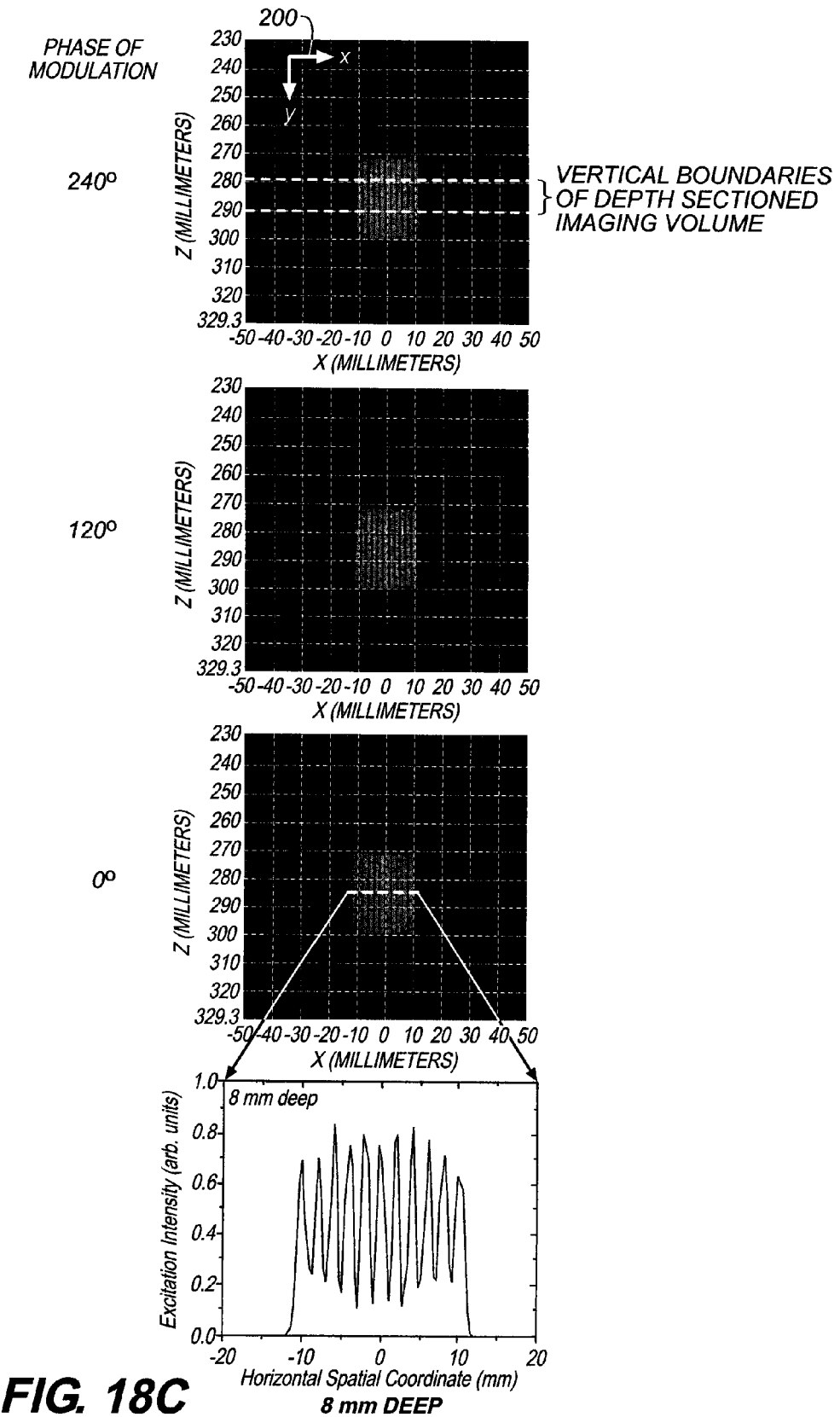
Figure 18D:
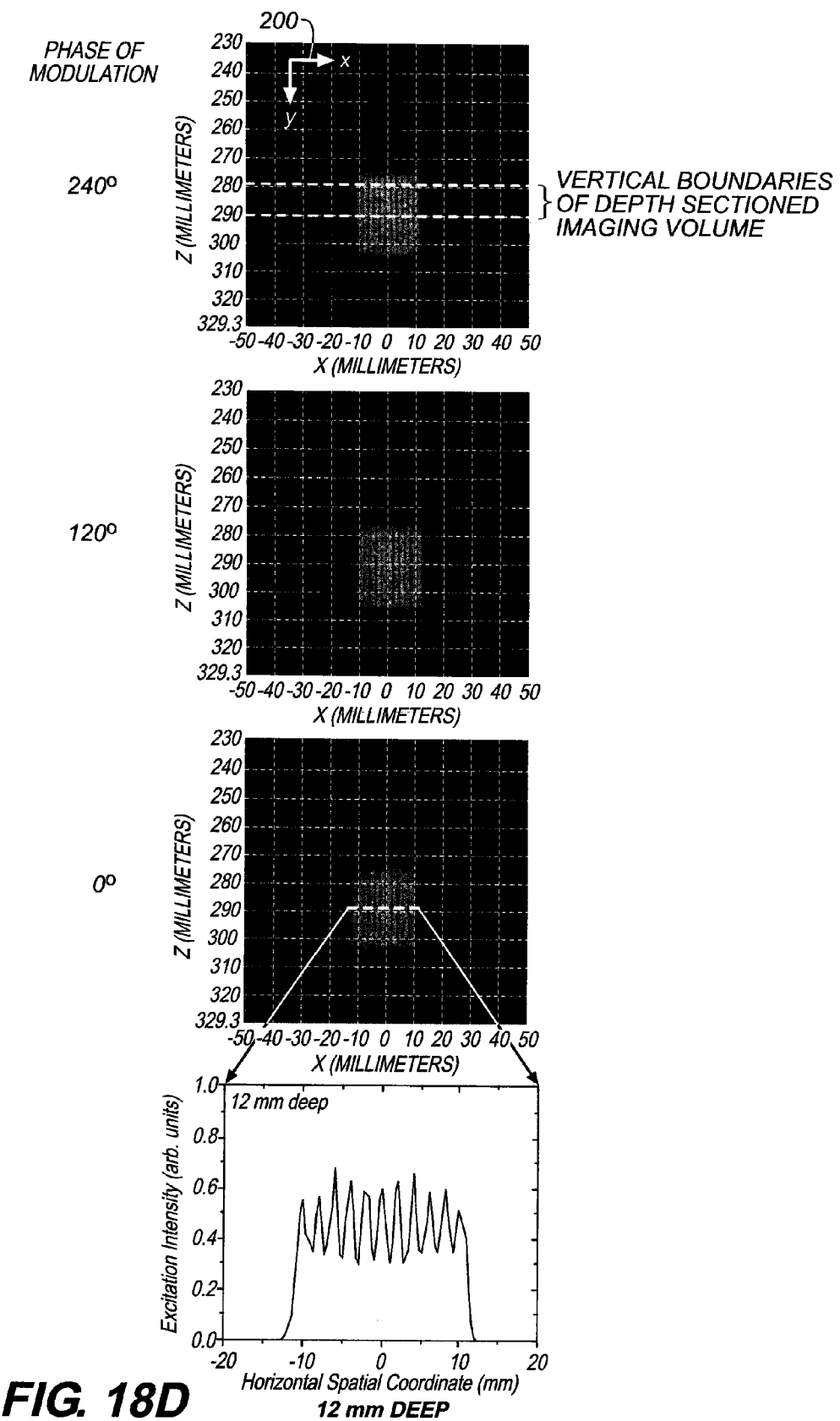
Figure 18E:
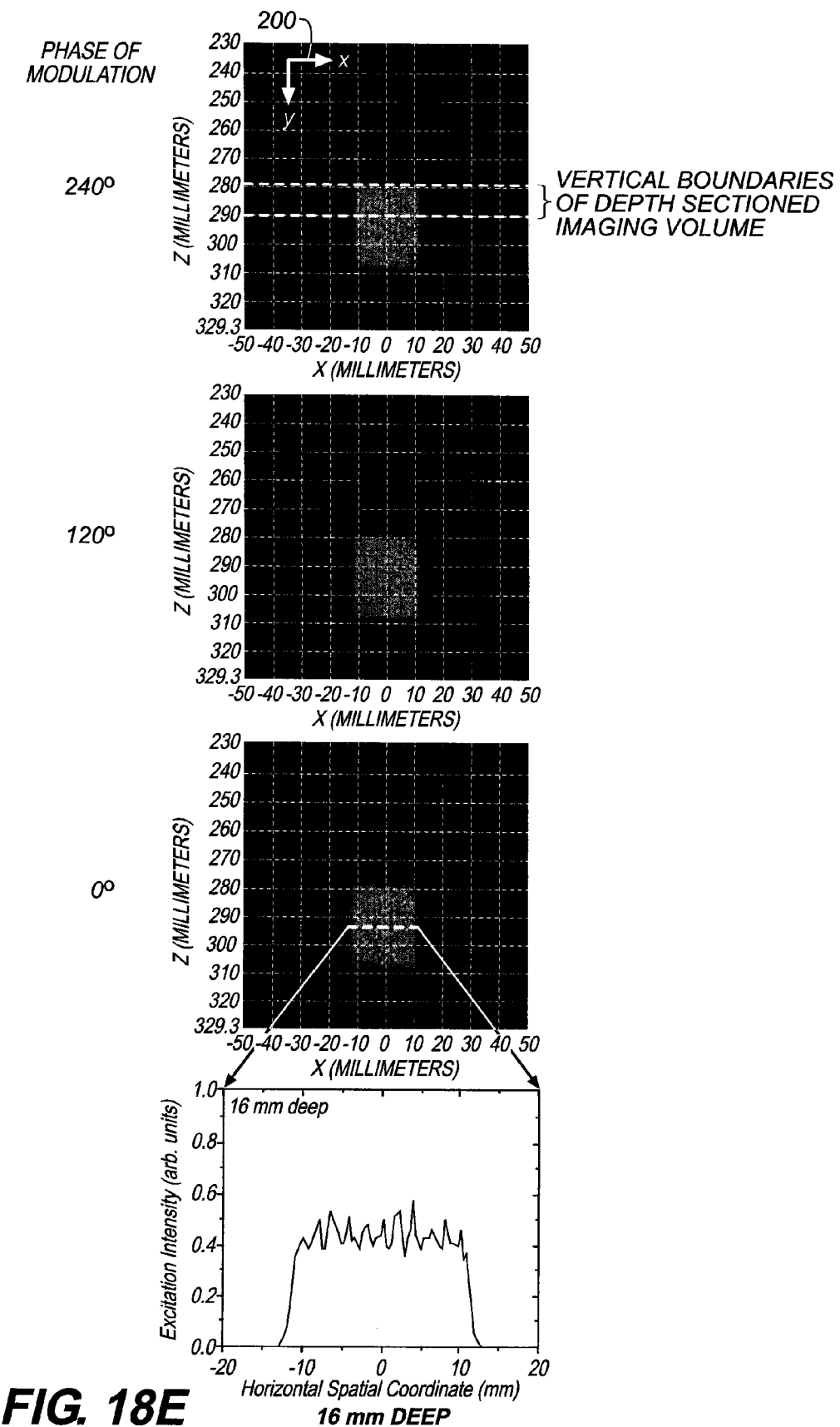

FIG. 16 shows a graphic representation of the workflow diagram of FIG. 11. The section representing steps 50a and 60a shows spatially modulated excitation radiation pattern 125a, b, and c delivered from direction "a" through beam path 110 to a hypothetical subject 131. Because the subject has topography, a shadow 132a is cast, thereby preventing depth sectioning in the shadowed region. The section representing steps 50b and 60b shows spatially modulated excitation radiation pattern 126a, b, and c delivered from direction "b" through beam path 111 to the hypothetical subject 131. A different shadow 132b is cast, but the region corresponding to shadow 132a is hereby illuminated. The section representing step 70 shows the coverage of bidirectional spatially modulated excitation radiation 127a, b, and c. The merger of the outputs of steps 60a and 60b provides full coverage of the subject area, in effect eliminating shadows.

FIG. 17 shows a cutaway perspective view of components of the image capture module 22 in accordance with a third embodiment of the present invention wherein spatially modulated excitation radiation is delivered from direction "a" using projection optics including a doubly telecentric Scheimpflug lens system 215. This embodiment is similar to the embodiment shown in FIG. 12, except the non-telecentric Scheimpflug lens systems 115 and 116 have been replaced with doubly telecentric Scheimpflug lens systems 215 and 216, respectively. In the embodiment shown, the doubly telecentric Scheimpflug lens systems each include two lens groups as indicated; however, generally more than two lens groups may comprise a doubly telecentric Scheimpflug lens system. By "doubly telecentric", it is meant that the lens system provides both object space telecentricity and image space telecentricity. The lens system delivers the spatially modulated excitation radiation through a beam path 210 to the surface of the platen 120 located at the image plane of the lens system, i.e., the X-Y plane. Upon reaching the platen surface, the spatially modulated excitation radiation 225a, b, and c, propagates further into the space beyond the platen, i.e., into the image space depth, which is the positive Z direction. The image space of the excitation Scheimpflug lens system is the object space of the fluorescence detection lens system, whereby the fluorescence signal is imaged through a beam path 235 by the detection lens system described previously. The excitation radiation is reflected along a direction indicated by the arrow 102; therefore, the excitation radiation is reflected away from the detection beam path, thereby minimizing the potential for that excitation radiation to cause background in the fluorescence signal.

FIG. 18 shows optical simulation results generally representing the embodiment diagrammatically shown in FIG. 17, i.e., an embodiment based on a doubly telecentric Scheimpflug lens system. The optical simulation was executed using TracePro optical modeling software from Lambda Research Corporation. A spatial modulation grid pitch of 2 mm, a matched pair of achromatic doublet lenses with 100 mm focal length (Edmund Optics, Inc., stock number NT49-390) as the doubly telecentric Scheimpflug lens system, an object plane-to-lens distance of 100 mm, an image plane-to-lens distance of 100 mm, and a lens-to-lens separation of 194 mm, were used in the simulation. The optical simulation results include the spatially modulated excitation radiation patterns present at a series of planes, parallel to the X-Y image plane, distributed through the image space depth beyond the platen, i.e., in the positive Z direction. Three different spatial modulation phases are shown for each depth. Whereas the diagrams of the spatially modulated excitation radiation pattern 225*a*, *b*, and *c* show an undersized round excitation radiation beam intersecting the spatial modulation grid, the optical simulations were performed using an excitation radiation beam that fills the spatial modulation grid so as to more clearly illustrate the absence of distortion inherent to a doubly telecentric Scheimpflug lens system and to compare with the optical simulation results shown in FIG. 9. Specifically, the transverse magnification provided by the doubly telecentric Scheimpflug lens system does not exhibit a gradient in the Y direction, i.e., along the direction parallel to the direction of the projection of the excitation radiation propagation vector onto the X-Y image plane, unlike the non-telecentric Scheimpflug lens system. Furthermore, the transverse magnification provided by the doubly telecentric Scheimpflug lens system does not exhibit a gradient along the Z direction, normal to the image plane, unlike the non-telecentric Scheimpflug lens system. As in the simulations for the non-telecentric Scheimpflug lens system shown in FIG. 9, in these simulations, the best focus is at 0 mm, defined as the platen surface. Similarly to the simulations for the non-telecentric Scheimpflug lens system shown in FIG. 9, these simulations show that the depth of modulation of the excitation radiation pattern decreases with increasing depth into the image space beyond the platen surface; i.e., the pattern is going out of focus. As in the simulations for the non-telecentric Scheimpflug lens system shown in FIG. 9, these simulations were performed for the case where the medium in the image space beyond the platen is not turbid; if the medium were instead turbid, then the turbidity would accelerate the decrease of the depth of modulation of the excitation radiation pattern with increasing depth into the image space beyond the platen surface. Similarly to FIG. 9, the profiles taken along the X direction, i.e., along the direction perpendicular to the direction of the projection of the excitation radiation propagation vector onto the image plane, further illustrate the decrease of the depth of modulation, defined as the ratio of the amplitude of the spatial oscillation, i.e., AC, to the average, i.e., DC, level, of the excitation radiation pattern with increasing depth into the image space beyond the platen surface. Unlike the simulations for the non-telecentric Scheimpflug lens system shown in FIG. 9, however, these profiles illustrate little decrease in the DC level of the excitation radiation pattern with increasing depth into the image space beyond the platen surface due to the constancy of the transverse magnification with depth, i.e., the excitation radiation does not spread out over a larger area. Similarly to the simulations for the non-telecentric Scheimpflug lens system shown in FIG. 9, these simulations also show that the spatially modulated excitation radiation pattern shifts in the positive Y direction, away from the object plane of the doubly telecentric Scheimpflug lens system, with increasing depth into the image space beyond the platen surface. As described previously, this shifting behavior also restricts the field of view of depth sectioning to that between the maximum Y extent of the X-Y image plane and the minimum Y extent of the deepest plane (shown by example as 16 mm deep).

FIG. 19 shows a summarized comparison of the depth-of-modulation response from the optical simulation results of FIGS. 9 and 18. The depth of modulation was calculated from sinusoidal fits to profiles from the optical simulations described previously. It is advantageous to have a steep decline in depth of modulation with increasing depth into the image space beyond the platen surface in order to achieve high depth-sectioning resolution. The comparison shows that the modeled doubly telecentric Scheimpflug lens system exhibits a steeper decline of depth of modulation with increasing depth into the image space beyond the platen surface than does the modeled non-telecentric Scheimpflug lens system. This is in large part because the focal length of the image lens of the modeled doubly telecentric Scheimpflug lens system is shorter than the modeled non-telecentric Scheimpflug lens system, so that the depth of focus of the modeled doubly telecentric Scheimpflug lens system is less than the modeled non-telecentric Scheimpflug lens system. The difference in the depth-of-modulation response shown here is not inherently characteristic of the non-telecentric and doubly telecentric Scheimpflug lens systems.

Figure 20:
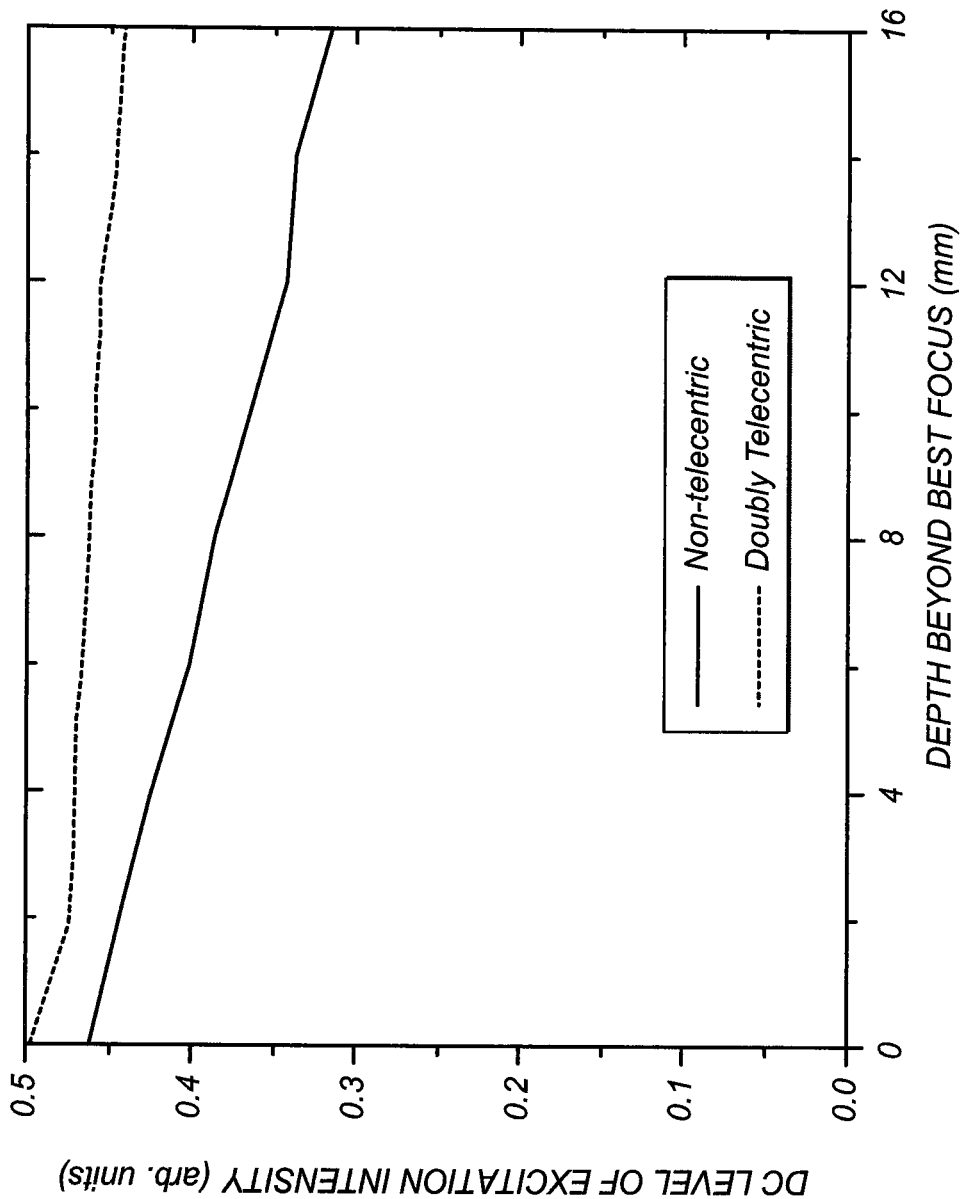
FIG. 20 shows a summarized comparison of the DC-level response from the optical simulation results of FIGS. 9 and 18.

FIG. 20 shows a summarized comparison of the DC-level response from the optical simulation results of FIGS. 9 and 18. The DC level was calculated from sinusoidal fits to profiles from the optical simulations described previously. It is advantageous to have a high DC level with increasing depth into the image space beyond the platen surface in order to achieve high depth-sectioning signal. The comparison shows that the modeled doubly telecentric Scheimpflug lens system maintains a high DC level with increasing depth into the image space beyond the platen surface than does the modeled non-telecentric Scheimpflug lens system. This is due to the constancy of the transverse magnification with depth inherently characteristic of the doubly telecentric Scheimpflug lens system as opposed to the increase of the transverse magnification with depth of inherently characteristic of the non-telecentric Scheimpflug lens system.

Figure 21:
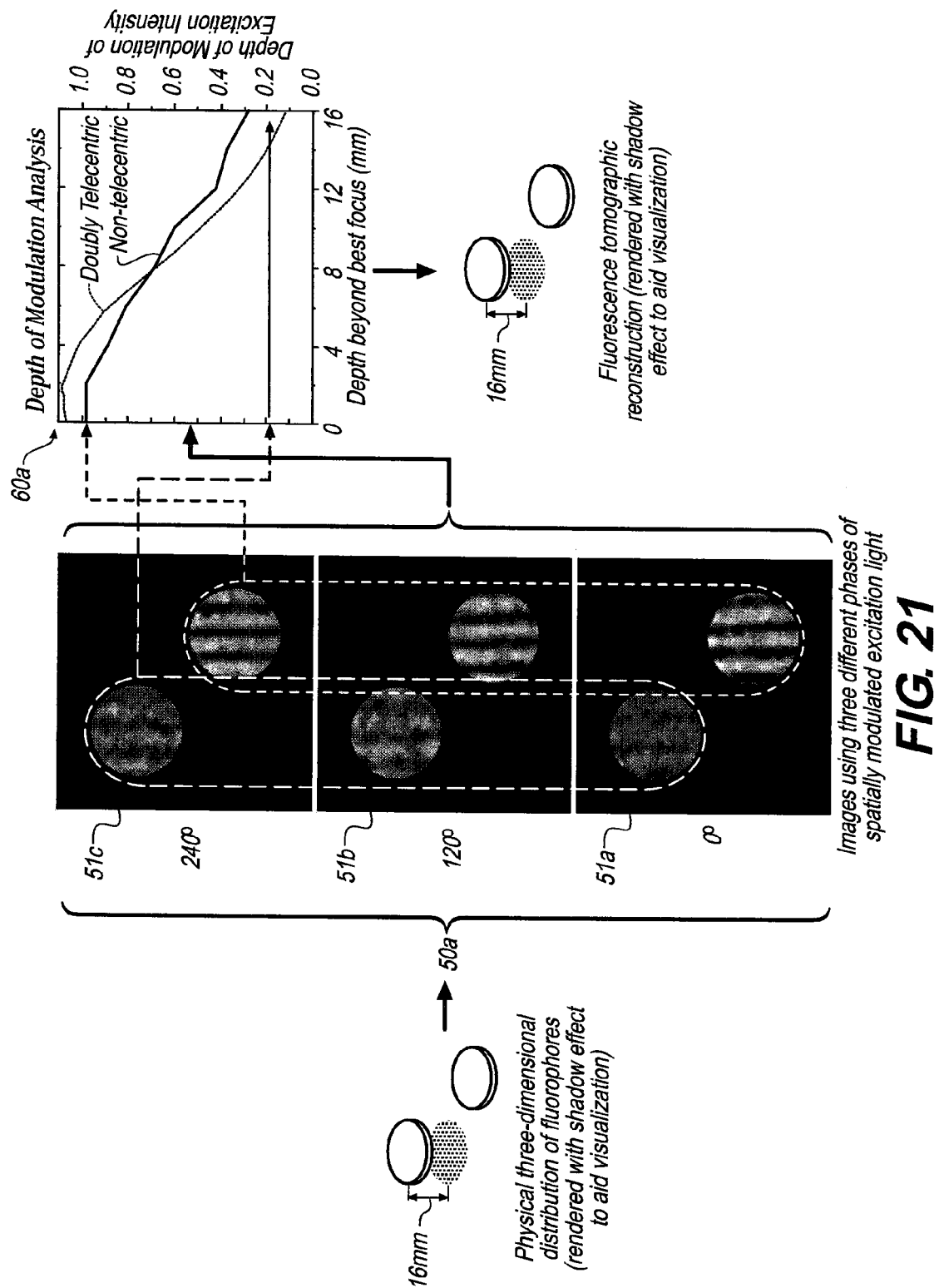
FIG. 21 shows a graphic representation of the workflow diagrams of FIGS. 5 and 6.

FIG. 21 shows a graphic representation of the workflow diagrams of FIGS. 5 and 6. A physical three-dimensional distribution of fluorophores is shown at left. The distribution includes two parallel discs: one at 0 mm, i.e., at the platen surface; the other raised 16 mm above the platen surface; and non-overlapping when viewed from the normal direction (the raised disc is shown northwest of the 0 mm disc). The simulated images represent step 50*a* wherein a fluorescence image set is acquired using a plurality of phases of spatially modulated excitation radiation delivered from direction "a", wherein the plurality of phases includes three relative phases, specifically 0 degrees step 51*a*, 120 degrees 51*b*, and 240 degrees 51*c*, i.e., one-third steps of the spatial modulation period length. The simulated images show that the depth of modulation of the 0 mm disc fluorescence is greater than the depth of modulation of the 16 mm disc fluorescence. The depth of modulation graph of FIG. 19 represents step 60*a* wherein depth sectioning is performed based on the depth of modulation in the fluorescence images. The high depth-of-modulation content in the image set is mapped to 0 mm depth whereas the low depth-of-modulation content in the image set is mapped to 16 mm. The output of step 60*a* is the fluorescence tomographic reconstruction of the physical three-dimensional distribution of fluorophores.

Figure 22:
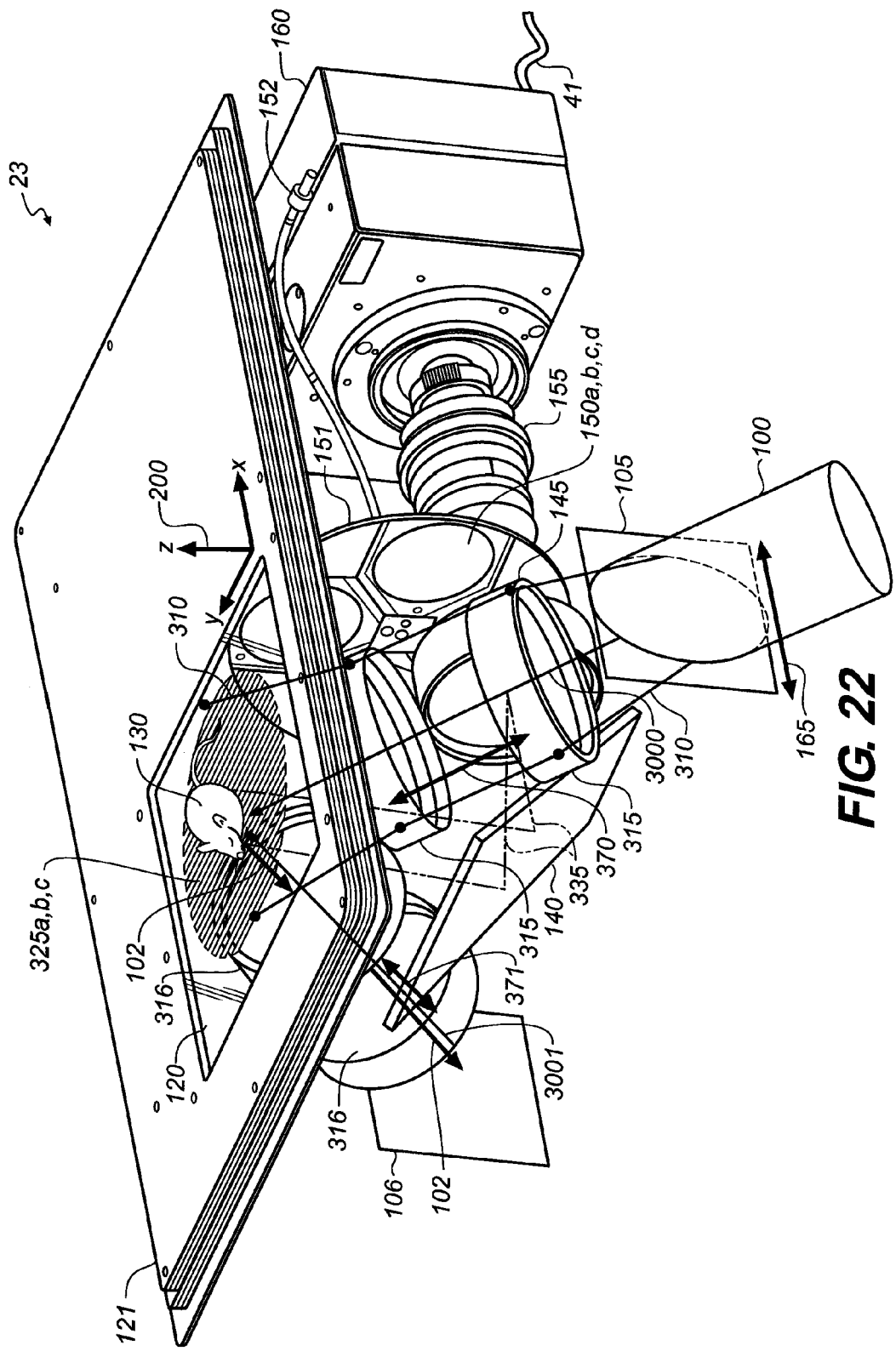
FIG. 22 shows a cutaway perspective view of components of the image capture module of the imaging system of FIG. 1 in accordance with a fourth embodiment of the present invention wherein spatially modulated excitation radiation is delivered from direction "a" using a doubly telecentric Scheimpflug zoom lens system configured for high magnification.
Figure 23:
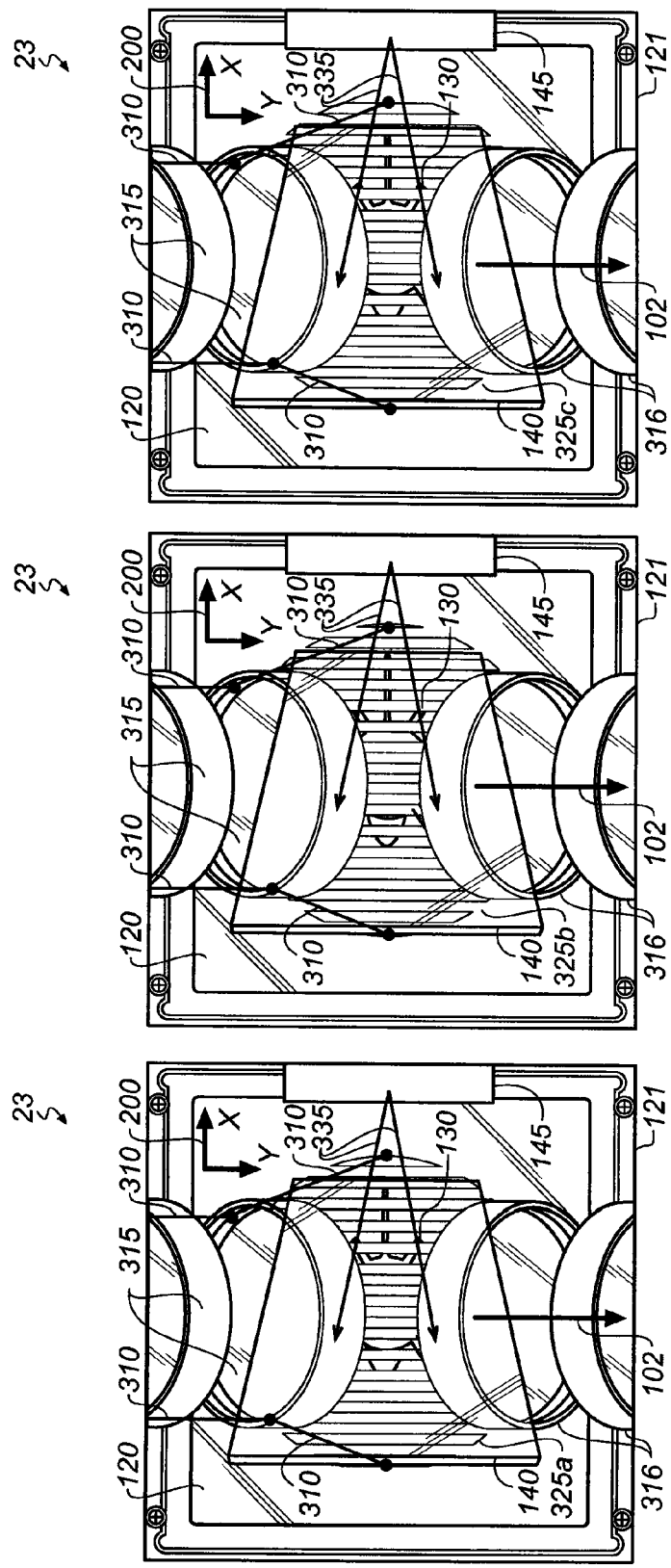
FIGS. 23A, 23B and 23C show cutaway diagrammatic views of the image capture module configured according to FIG. 22.

FIG. 22 shows a cutaway perspective view of components of the image capture module 23 of the imaging system 1 in accordance with a fourth embodiment of the present invention wherein spatially modulated excitation radiation is delivered from direction "a" using projection optics including a doubly telecentric Scheimpflug zoom lens system 315 configured for high magnification. This embodiment is similar to the embodiment shown in FIG. 17, except the doubly telecentric Scheimpflug lens systems 215 and 216 have been replaced with doubly telecentric Scheimpflug zoom lens systems 315 and 316, respectively. In the embodiment shown, the doubly telecentric Scheimpflug zoom lens systems each include two lens groups as indicated; however, generally more than two lens groups may comprise a doubly telecentric Scheimpflug zoom lens system. One of ordinary skill in the art will understand that a plurality of doubly-telecentric fixed-focal lens systems providing different magnifications would provide equivalent benefits as a doubly telecentric zoom lens system. The lens system delivers the spatially modulated excitation radiation through a beam path 310 to the surface of the platen 120 located at the image plane of the lens system, i.e., the X-Y plane. Upon reaching the platen surface, the spatially modulated excitation radiation 325*a, b*, and *c*, propagates further into the space beyond the platen, i.e., into the image space depth, which is the positive Z direction. The image space of the excitation Scheimpflug lens system is the object space of the fluorescence detection lens system, whereby the fluorescence signal is imaged through a beam path 335 by the detection lens system described previously. The excitation radiation is reflected along a direction indicated by the arrow 102; therefore, the excitation radiation is reflected away from the detection beam path, thereby minimizing the potential for that excitation radiation to cause background in the fluorescence signal. FIGS. 23A, 23B and 23C show cutaway diagrammatic views of the image capture module 23 configured according to FIG. 22. FIGS. 23A, 23B and 23C are similar to FIGS. 7A, 7B and 7C, except the spatial frequency of the excitation radiation modulation has decreased due to the high magnification configuration of the zoom lens system. The zoom lens system provides an alternative means for adjusting the spatial frequency of the excitation radiation modulation compared to that shown in FIG. 4.

Figure 24:
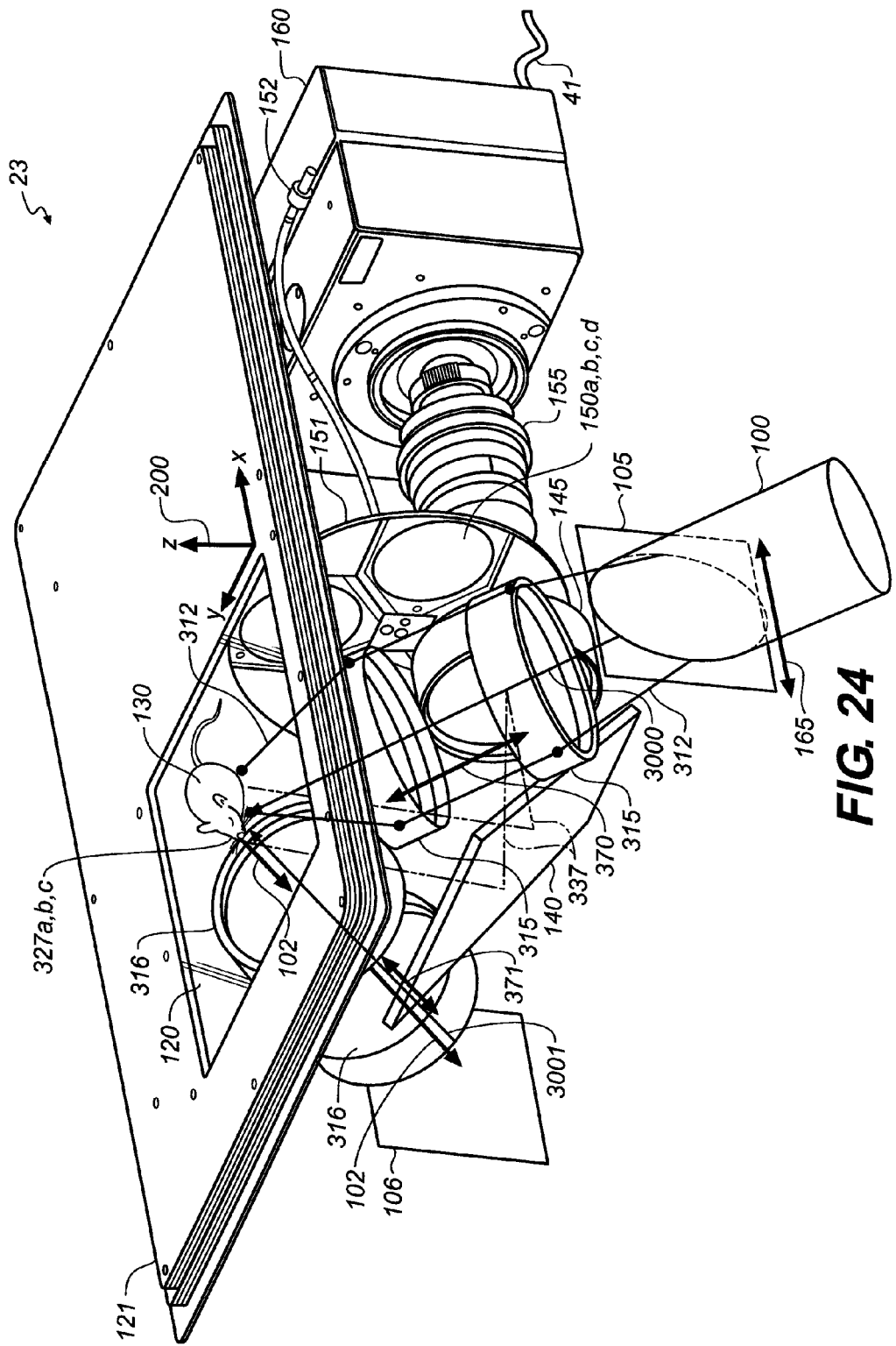
FIG. 24 shows a cutaway perspective view of the image capture module of FIG. 22 but instead configured for low magnification.
Figure 25:
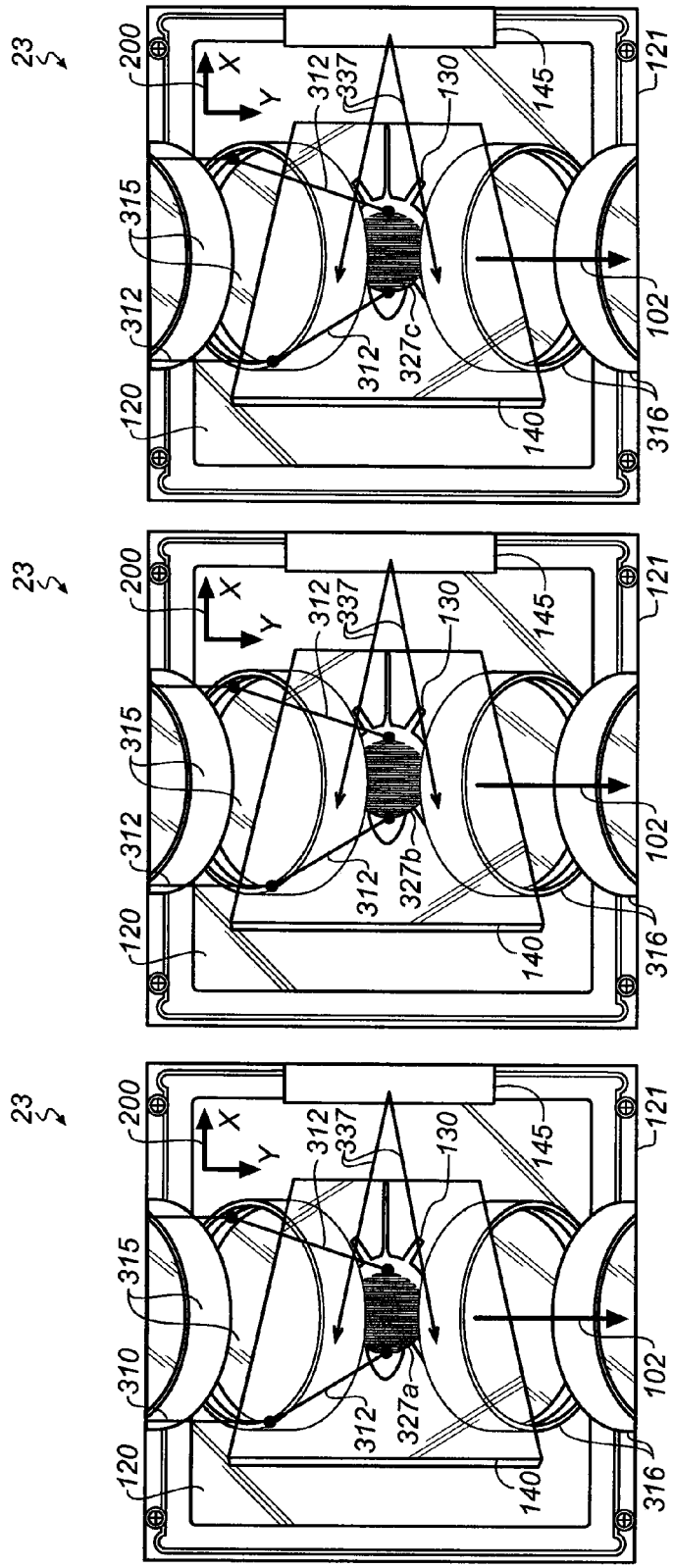
FIGS. 25A, 25B and 25C show cutaway diagrammatic views of the image capture module configured according to FIG. 24.

FIG. 24 shows a cutaway perspective view of the image capture module 23 of FIG. 22 but instead configured for low magnification. The lens system delivers the spatially modulated excitation radiation through a beam path 312 to the surface of the platen 120 located at the image plane of the lens system, i.e., the X-Y plane. Upon reaching the platen surface, the spatially modulated excitation radiation 327*a, b*, and *c*, propagates further into the space beyond the platen, i.e., into the image space depth, which is the positive Z direction. The image space of the excitation Scheimpflug lens system is the object space of the fluorescence detection lens system, whereby the fluorescence signal is imaged through a beam path 337 by the detection lens system described previously. The excitation radiation is reflected along a direction indicated by the arrow 102; therefore, the excitation radiation is reflected away from the detection beam path, thereby minimizing the potential for that excitation radiation to cause background in the fluorescence signal. FIGS. 25A, 25B and 25C show cutaway diagrammatic views of the image capture module 23 configured according to FIG. 24. FIGS. 25A, 25B and 25C are similar to FIGS. 23A, 23B and 23C, except the spatial frequency of the excitation radiation modulation has increased due to the low magnification configuration of the zoom lens system.

Figure 26:
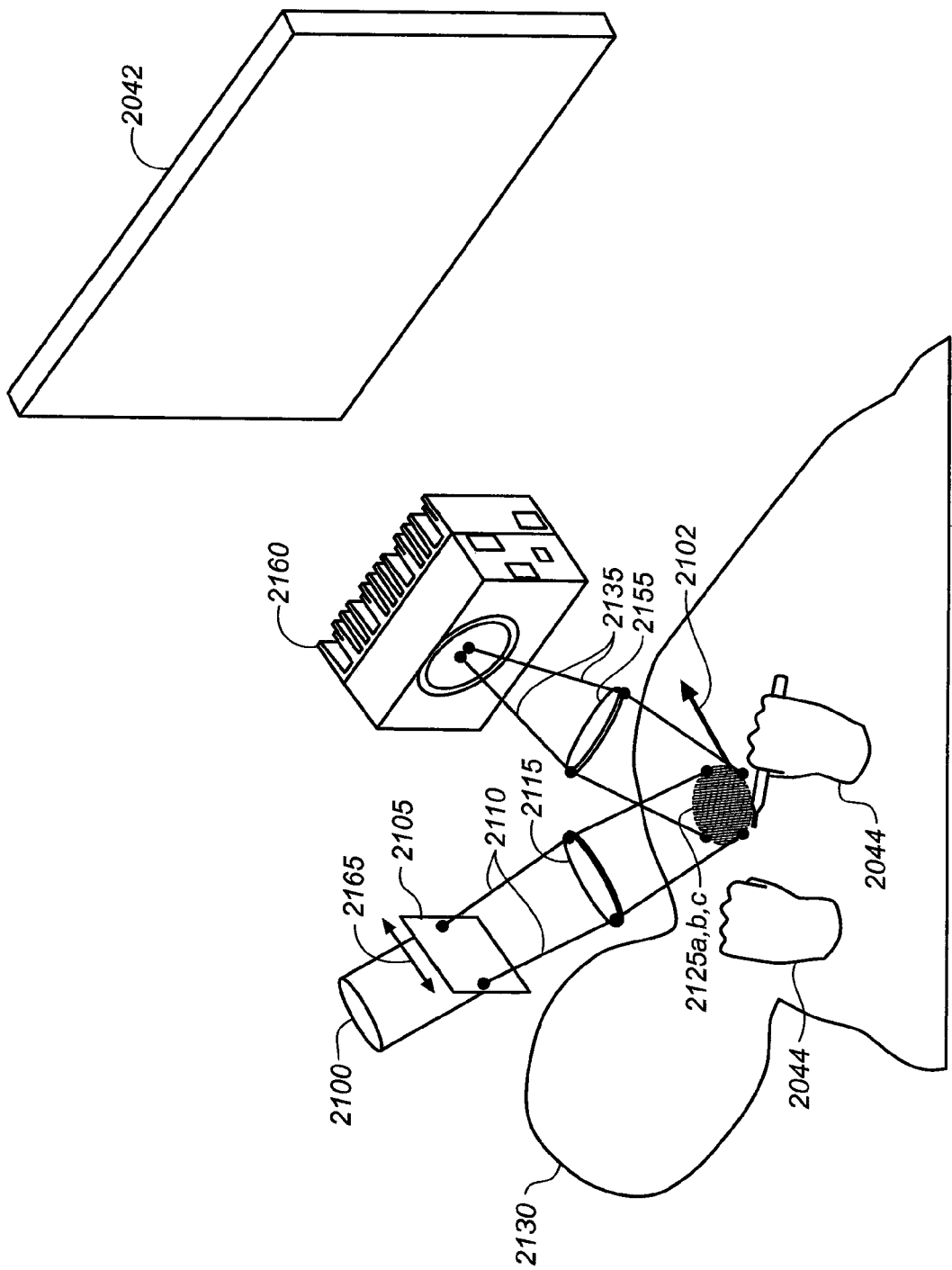
FIG. 26 shows a cutaway perspective view of components of another exemplary electronic imaging system in accordance with a fifth embodiment of the present invention wherein the optical plane of the excitation source and the optical plane of the object are subject to a Scheimpflug condition provided by projection optics, and the optical plane of the object and the optical plane of the camera image are also subject to a Scheimpflug condition provided by imaging optics, whereby the optical plane of the excitation source and the optical plane of the camera image are orthogonal.
Figure 27:
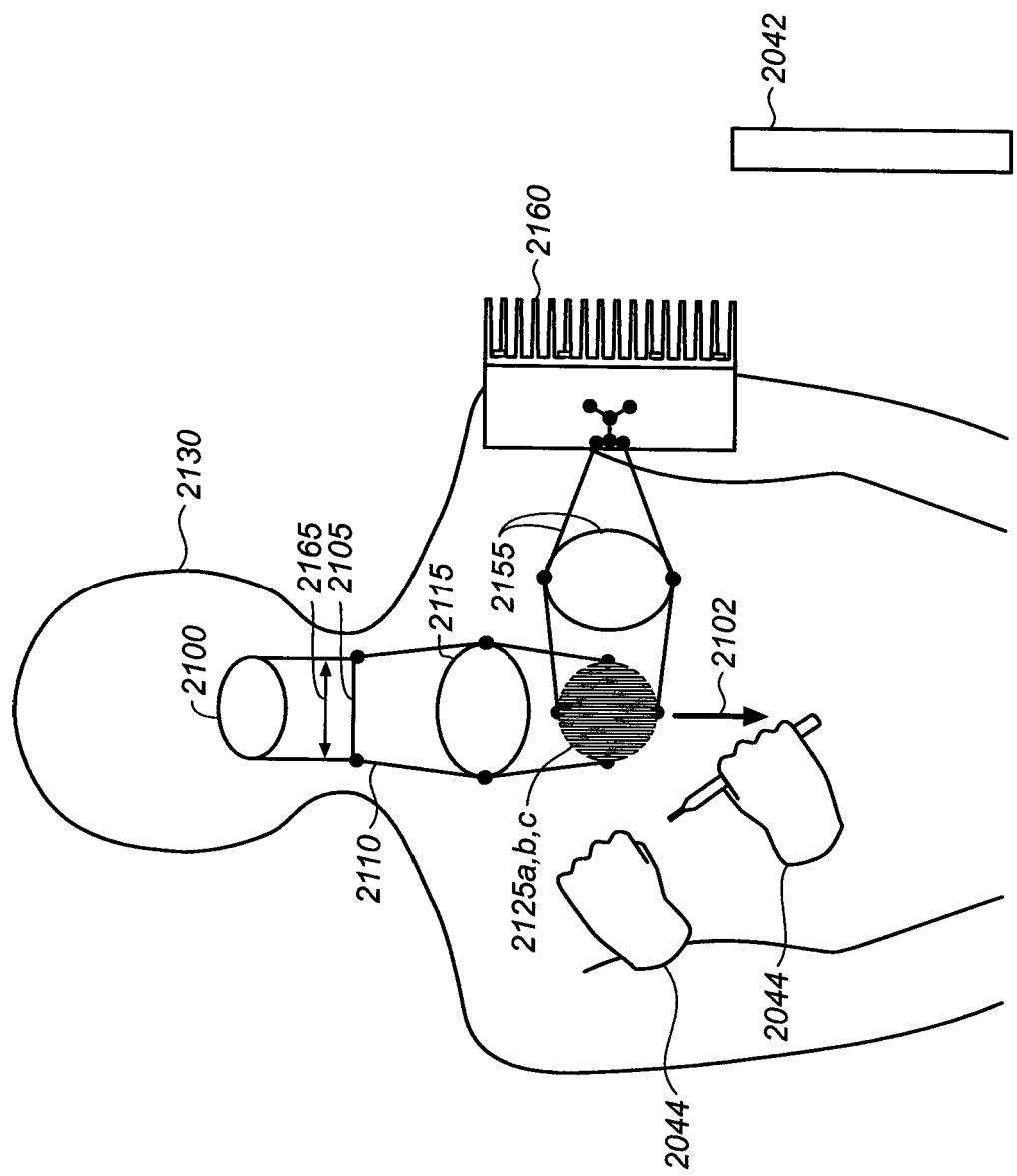
FIG. 27 shows a cutaway perspective view of the electronic imaging system of FIG. 26.

FIGS. 26 and 27 show cutaway perspective views of components of another exemplary electronic imaging system in accordance with a fifth embodiment of the present invention. The optical plane of the excitation source and the optical plane of the object are subject to a Scheimpflug condition provided by projection optics. The optical plane of the object and the optical plane of the camera image are also subject to a Scheimpflug condition provided by imaging optics. As a result, the optical plane of the excitation source and the optical plane of the camera image are orthogonal. Excitation radiation 2100 is transmitted through a one-dimensional spatial modulation grid 2105. The spatial modulation grid is located at the object plane of a Scheimpflug lens system 2115. In the embodiment shown, the Scheimpflug lens system includes a single lens group as indicated; however, generally more than one lens group may comprise a Scheimpflug lens system. The Scheimpflug lens system may be either non-telecentric or telecentric as described previously. The spatial modulation grid is configurable to produce a plurality of phases that shift along the direction indicated by arrow 2165. The lens system delivers the spatially modulated excitation radiation through a beam path 2110 to the surface of an immobilized subject, such as an anesthetized human patient 2130 undergoing surgery who has been administered a fluorescent probe, located at the image plane of the lens system, i.e., the X-Y plane. By definition, a Scheimpflug lens system forms an image of an object whereby the object and image planes are not parallel to each other, but are instead inclined with respect to each other. Upon reaching the subject surface, the spatially modulated excitation radiation 2125*a, b*, and *c*, propagates further into the space beyond the object surface, i.e., into the image space depth, which is the positive Z direction. The characteristics of the spatial profile of the excitation radiation, such as the depth of modulation and DC level, at the various planes, parallel to the X-Y image plane, through the image space depth depend on both the image forming properties of the lens system, such as the depth of focus, as well as the optical properties, such as the turbidity, of the medium in the image space. The immobilized subject 2130 fills the image space with a turbid medium and provides a spatially distributed fluorescence signal with spatial modulation in proportion to the spatially modulated excitation radiation through the image space. The image space of the excitation Scheimpflug lens system is the object space of the fluorescence detection Scheimpflug lens system. The fluorescence signal is imaged through a beam path 2135 by a detection Scheimpflug lens system including a detection lens 2155, onto a sensor in a digital camera 2160, such as a thermoelectrically cooled charge coupled device camera, and an emission filter wheel (not shown), containing a plurality of emission filters provides spectral selection of the fluorescence signal as well as rejection of excitation radiation from the sensor. The excitation radiation is reflected along a direction indicated by the arrow 2102; therefore, the excitation radiation is reflected away from the detection beam path, thereby minimizing the potential for that excitation radiation to cause background in the fluorescence signal. The orthogonality of the optical plane of the excitation source and the optical plane of the camera image substantially minimizes excitation radiation from reaching the detection beam path. Furthermore, because cost of the emission filters is increased and fluorescence transmission of the emission filters is decreased with increased rejection of the excitation radiation, the reflection of the excitation radiation away from the detection beam path enables low cost emission filtration with high transmission. The detected image of the fluorescent signal is displayed on display device 2042, as useful for fluorescent image guided surgery. The Scheimpflug arrangement of both the fluorescence excitation optics and the fluorescence imaging optics enables an accessible object space, such as would be desirable for fluorescence image guided surgery as shown by surgeon's hands 2044.

PARTS LIST

1 exemplary electronic imaging system
10 excitation radiation source
12 lamp unit
14 excitation filter wheel
16*a, b, c* excitation filters
20 image capture module
21 image capture module
22 image capture module 23 image capture module
30 sample cabinet
32 door
40 communications and computer control system
41 communication cable
42 display device or monitor
50a, b step
51a, b, c step
60a, b step
70 step
100 excitation radiation from direction "a"
101 excitation radiation from direction "b"
102 direction of reflection of excitation radiation from direction "a"
103 direction of reflection of excitation radiation from direction "b"
105 spatial modulation grid
106 spatial modulation grid
110 beam path of spatially modulated excitation radiation delivered from direction "a"
111 beam path of spatially modulated excitation radiation delivered from direction "b"
115 non-telecentric Scheimpflug lens system
116 non-telecentric Scheimpflug lens system
120 optically transparent platen
121 subject stage
125a, b, c spatially modulated excitation radiation pattern delivered from direction "a"
126a, b, c spatially modulated excitation radiation pattern delivered from direction "b"
127a, b, c coverage of bi-directional spatially modulated excitation radiation
130 anesthetized mouse
131 hypothetical subject
132a, b shadow
135 beam path of fluorescence detection
136 beam path of fluorescence detection
140 folding mirror
145 detection lens diopter
150a, b, c, d emission filters
151 emission filter wheel
152 emission filter wheel actuator
155 detection lens
160 digital camera
165 direction to produce spatial phase shift
166 direction to produce spatial phase shift
200 X-Y-Z coordinate system
205 slider with plurality of spatial modulation grids
206 spatial modulation grid with "high" spatial modulation frequency
207 spatial modulation grid with "medium" spatial modulation frequency
208 spatial modulation grid with "low" spatial modulation frequency
210 beam path of spatially modulated excitation radiation delivered from direction "a"
215 doubly telecentric Scheimpflug lens system
216 doubly telecentric Scheimpflug lens system
225a, b, c spatially modulated excitation radiation pattern delivered from direction "a"
235 beam path of fluorescence detection
310 beam path of spatially modulated excitation radiation delivered from direction "a"
312 beam path of spatially modulated excitation radiation delivered from direction "a"
315 doubly telecentric Scheimpflug zooming lens system
316 doubly telecentric Scheimpflug zooming lens system
325a, b, c spatially modulated excitation radiation pattern delivered from direction "a"
327a, b, c spatially modulated excitation radiation pattern delivered from direction "a"
335 beam path of fluorescence detection
337 beam path of fluorescence detection
1050 transparent stripes
1051 non-transparent stripes
1052 spatial modulation period
2042 display device or monitor
2044 surgeon's hands
2100 excitation radiation
2102 direction of reflection of excitation radiation
2105 spatial modulation grid
2110 beam path of spatially modulated excitation radiation
2115 Scheimpflug excitation lens system
2125a, b, c spatially modulated excitation radiation pattern
2130 anesthetized human patient
2165 direction to produce spatial phase shift
2135 beam path of fluorescence detection
2155 Scheimpflug detection lens system
2160 digital camera

What is claimed is:

1. An apparatus for quantitative modulated fluorescence imaging to perform depth sectioned fluorescence imaging of a turbid sample including a fluorescent turbid medium, the apparatus comprising:
    projection optics, including a first optical axis, to expose the turbid sample to a periodic pattern of excitation radiation from an energy source to provide depth-resolved discrimination of fluorescent structures within the turbid medium;
    an image capture module, including a second optical axis and a detection beam path, to receive a data image from the sample, whereby the first optical axis is inclined relative to the second optical axis;
    a signal processor to transform the data image from the sample, spatially filter the transformed data image from the sample, and reconstruct the filtered, transformed data image from the sample;
    the projection optics including an object plane and an image plane that are subject to a Scheimpflug condition;
    the periodic pattern of excitation radiation having periodicity in a direction perpendicular to a direction of a projection of the first optical axis onto the image plane, so that the phase of the periodic pattern of excitation radiation does not change with increasing depth into an image space; and
    the projection optics having an angle of inclination relative to an image plane of the apparatus, the angle of inclination being selected such that the component of excitation radiation incident upon the sample that is not absorbed by the sample is scattered in such a way that substantially reduces excitation radiation from reaching the detection beam path.

2. The apparatus of claim 1, wherein the projection optics comprise one or more non-telecentric Scheimpflug lens systems.

3. The apparatus of claim 2, wherein the projection optics comprise two non-telecentric Scheimpflug lens systems that are mirror-symmetric.

4. The apparatus of claim 2, wherein the one or more non-telecentric Scheimpflug lens systems are zoomable.

5. The apparatus of claim 2, wherein the one or more non-telecentric Scheimpflug lens systems include a plurality of fixed-focal lens systems, each providing a different magnification.

6. The apparatus of claim 1, wherein the projection optics comprise one or more Scheimpflug lens systems providing object space telecentricity.

7. The apparatus of claim 6, wherein the projection optics comprise two Scheimpflug lens systems providing object space telecentricity that are mirror-symmetric.

8. The apparatus of claim 6, wherein the one or more Scheimpflug lens systems providing object space telecentricity are zoomable.

9. The apparatus of claim 6, wherein the one or more Scheimpflug lens systems providing object space telecentricity include a plurality of fixed-focal lens systems each providing a different magnification.

10. The apparatus of claim 1, wherein the projection optics comprise one or more Scheimpflug lens systems providing image space telecentricity.

11. The apparatus of claim 10, wherein the projection optics comprise two Scheimpflug lens systems providing image space telecentricity that are mirror-symmetric.

12. The apparatus of claim 10, wherein the Scheimpflug lens systems providing image space telecentricity are zoomable.

13. The apparatus of claim 10, wherein the one or more Scheimpflug lens systems providing image space telecentricity include a plurality of fixed-focal lens systems each providing a different magnification.

14. The apparatus of claim 1, wherein the projection optics comprise one or more doubly telecentric Scheimpflug lens systems.

15. The apparatus of claim 14, wherein the projection optics comprise two doubly telecentric Scheimpflug lens systems that are mirror-symmetric.

16. The apparatus of claim 14, wherein the doubly telecentric Scheimpflug lens system(s) is (are) zoomable.

17. The apparatus of claim 1, further comprising detection optics including an object plane and an optical plane of a camera image that are subject to a Scheimpflug condition.

18. The apparatus of claim 1, further comprising image detection optics including a first optical plane of the sample and a second optical plane of images captured by the image capture module, the first and second optical planes being subject to a Scheimpflug condition.

19. An apparatus for quantitative modulated fluorescence imaging to perform depth sectioned fluorescence imaging of a turbid sample including a fluorescent turbid medium, the apparatus comprising:
projection optics, including a first optical axis, to expose the turbid sample to a periodic pattern of excitation radiation to provide depth-resolved discrimination of fluorescent structures within the turbid medium;
an image capture module, including a second optical axis and a detection beam path, to receive a data image from the sample, whereby the first optical axis is inclined relative to the second optical axis;
a signal processor to transform the data image from the sample, spatially filter the transformed data image from the sample, and reconstruct the filtered, transformed data image from the sample;
the projection optics including an object plane and an image plane that are subject to a Scheimpflug condition; and
the projection optics having an angle of inclination relative to an image plane of the apparatus, the angle of inclination being selected such that the component of excitation radiation incident upon the sample that is not absorbed by the sample is scattered in such a way that substantially reduces excitation radiation from reaching the detection beam path.

20. A method for quantitative modulated fluorescence imaging to perform depth sectioned fluorescence imaging of a turbid sample composed of a fluorescent turbid medium, comprising using a computer to perform steps of:
acquiring two or more fluorescence image sets from two or more sets of projection optics, whose optical axes have different angles of inclination relative to an optical axis of an image capture module, to provide coverage of regions shadowed, by sample topography, for any one set of projection optics; and
merging the two or more fluorescence image sets.

21. A method for performing depth sectioned fluorescence imaging of a turbid sample including a fluorescent turbid medium, using an apparatus for quantitative modulated fluorescence imaging, the apparatus including projection optics with a first optical axis, to expose the turbid sample to a periodic pattern of excitation radiation to provide depth-resolved discrimination of fluorescent structures within the turbid medium; an image capture module, including a second optical axis and a detection beam path, to receive a data image from the sample; a signal processor to transform the data image from the sample, spatially filter the transformed data image from the sample, and reconstruct the filtered, transformed data image from the sample, comprising the steps of:
inclining the first optical axis relative to the second optical axis;
providing in the projection optics an object plane and an image plane that are subject to a Scheimpflug condition; and
inclining the projection optics at an angle of inclination relative to an image plane of the apparatus, the angle of inclination being selected such that the component of excitation radiation incident upon a sample, previously provided, that is not absorbed by the sample is scattered in such a way that substantially reduces excitation radiation from reaching the detection beam path.

22. The method of claim 21, further comprising a step of providing the periodic pattern of excitation radiation with a periodicity in a direction perpendicular to a direction of the projection of the first optical axis onto the image plane, so that the phase of the periodic pattern of excitation radiation does not change with increasing depth into an image space.

* * * * *